US006289247B1

(12) United States Patent
Faltys et al.

(10) Patent No.: US 6,289,247 B1
(45) Date of Patent: Sep. 11, 2001

(54) STRATEGY SELECTOR FOR MULTICHANNEL COCHLEAR PROSTHESIS

(75) Inventors: Michael A. Faltys, Northridge; Carol Murad, Woodland Hills, both of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/322,712

(22) Filed: May 28, 1999

Related U.S. Application Data

(63) Continuation-in-part of application No. 09/251,760, filed on Feb. 18, 1999.
(60) Provisional application No. 60/087,656, filed on Jun. 2, 1998.

(51) Int. Cl.[7] .............................. A61F 2/18; H04R 25/00; A61N 1/00
(52) U.S. Cl. ................... 607/57; 607/55; 623/10
(58) Field of Search .................. 607/55–57; 623/10

(56) References Cited

U.S. PATENT DOCUMENTS

| 4,232,679 | 11/1980 | Schulman . |
| 4,532,930 | 8/1985 | Crosby et al. . |
| 4,577,641 | 3/1986 | Hochmair et al. . |
| 4,592,359 | 6/1986 | Galbraith . |

(List continued on next page.)

FOREIGN PATENT DOCUMENTS

| 0241101 | 4/1984 | (EP) . |
| 9501709 | 1/1995 | (WO) . |
| 9701314 | 1/1997 | (WO) . |
| 9709863 | 3/1997 | (WO) . |

Primary Examiner—Carl H. Layno

(74) Attorney, Agent, or Firm—Bryant R. Gold

(57) ABSTRACT

A universal strategy selector (USS) for use with a multichannel cochlear prosthesis includes: (a) a processor, or equivalent; (b) a selector; and (c) a display. The multichannel cochlear prosthesis is characterized by multiple stimulation channels through which a specific pattern of electrical stimulation, modulated by acoustic signals, and in accordance with a selected speech processing strategy, may be spatiotemporal applied to a patients cochlea in order to yield speech intelligibility. The processor of the USS includes appropriate processing means coupled to the multichannel cochlear prosthesis for defining one of a plurality of speech processing strategies for use by the multichannel cochlear prosthesis. In one embodiment, the processing means is realized using a personal computer (PC) programmed with appropriate software. The speech processing strategy that may be selected by the USS may be selected from a multiplicity of speech processing strategies. In one embodiment, the multiplicity of speech processing strategies includes at least one simultaneous speech processing strategy, such as simultaneous analog stimulation (SAS); and at least one non-simultaneous speech processing strategy, such as a continuous interleaved sampler (CIS); and at least one strategy whose temporal characteristics lie somewhere in between simultaneous or non-simultaneous, and whose stimulating waveform(s) may comprise a hybrid combination of analog and/or pulsatile waveforms. In another embodiment, the speech processing strategy that may be selected by the USS is selected from a plurality of speech processing strategies of the same type, e.g., pulsatile strategies. The selector of the USS comprises a switch, pointer, or other selection means, for manually selecting one of the multiplicity or plurality of speech processing strategies as the selected speech processing strategy. The display of the USS, which is controlled by the processing means, provides a graphical or visual representation that characterizes the selected speech processing strategy in terms of representative stimulation waveforms and electrode coupling (e.g., bipolar or monopolar) for each channel.

38 Claims, 19 Drawing Sheets

U.S. PATENT DOCUMENTS

| | | |
|---|---|---|
| 4,612,934 | 9/1986 | Borkan . |
| 4,617,913 | 10/1986 | Eddington . |
| 4,745,309 | 5/1988 | Waller, Jr. . |
| 4,901,353 | 2/1990 | Widin . |
| 4,947,844 | 8/1990 | McDermott . |
| 5,095,904 | 3/1992 | Seligman et al. . |
| 5,626,629 | 5/1997 | Faltys et al. .......................... 607/57 |
| 6,068,652 * | 5/2000 | Cohen et al. .......................... 607/57 |

* cited by examiner

SIMULTANEOUS ANALOG STIMULATION BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-875 | 875-1150 | 1150-1450 | 1450-2000 | 2000-2600 | 2600-3800 | 3800-6800 |
| 7 CHANNELS | 250-500 | 500-875 | 875-1150 | 1150-1450 | 1450-2000 | 2000-2600 | 2600-6800 | |
| 6 CHANNELS | 250-500 | 500-875 | 875-1150 | 1150-1750 | 1750-2600 | 2600-6800 | | |
| 5 CHANNELS | 250-500 | 500-875 | 875-1450 | 1450-2600 | 2600-6800 | | | |
| 4 CHANNELS | 250-875 | 875-1450 | 1450-2600 | 2600-6800 | | | | |
| 3 CHANNELS | 250-875 | 875-2600 | 2600-6800 | | | | | |
| 2 CHANNELS | 350-700 | 2200-4400 | | | | | | |
| 1 CHANNEL | 250-6800 | | | | | | | |

CIS BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-730 | 730-1015 | 1015-1450 | 1450-2000 | 2000-2600 | 2600-3800 | 3800-6800 |
| 7 CHANNELS | 250-500 | 500-730 | 730-1150 | 1150-1750 | 1750-2600 | 2600-3800 | 3800-6800 | |
| 6 CHANNELS | 250-580 | 580-875 | 875-1450 | 1450-2000 | 2000-3300 | 3300-6800 | | |
| 5 CHANNELS | 250-580 | 580-1015 | 1015-1750 | 1750-3300 | 3300-6800 | | | |
| 4 CHANNELS | 250-730 | 730-1450 | 1450-2600 | 2600-6800 | | | | |
| 3 CHANNELS | 250-875 | 875-2000 | 2000-6800 | | | | | |
| 2 CHANNELS | 350-700 | 2200-4400 | | | | | | |
| 1 CHANNEL | 250-6800 | | | | | | | |

FIG. 3C

STRATEGY SELECTOR FOR MULTICHANNEL COCHLEAR PROSTHESIS

This application is a continuation-in-part (CIP) of U.S. application Ser. No. 09/251,760 filed 02/18/1999; and claims the benefit of U.S. provisional application Ser. No. 60/087,656, filed 06/02/1998; both of which applications are incorporated herein by reference. The invention described in this application is further related to the invention described in copending patent application Ser. No. 09/322,711, filed concurrently herewith, entitled "Multichannel Cochlear Prosthesis With Flexible Control of Stimulus Waveforms", which application is also incorporated herein by reference.

BACKGROUND OF THE INVENTION

The present invention relates to multichannel cochlear prosthesis, and more particularly to a multichannel cochlear prosthesis that offers selectable and flexible control of a full spectrum of stimulus waveforms that are applied to the cochlea through each of the channels of the system.

Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a so-called speech processor that is programmed to meet the particular requirements of each patient. Several different schemes for processing the acoustic signal and transforming it into electrical stimuli have been developed and are well-described in the scientific literature and various patents. These schemes can generally be divided into two basic types on the basis of the waveforms of the electrical stimuli:

i) Analog waveforms, which are essentially filtered versions of the continuous acoustic waveform, usually involving dynamic range compression, bandpass filtering and scaling to the stimulus current ranges that evoke a satisfactory range of auditory sensations from threshold of perception to maximal comfortable loudness. This produces a rich but poorly controlled set of resultant waveforms because, inter alia, the waveforms are susceptible to degradation by an electrode array that does not have fully isolated channels.

ii) Biphasic pulses, or, in more general terms, multiphasic pulses. Biphasic pulses consist of a single cycle of a pulsed wave in which current flows in one direction at a specified magnitude and for a specified brief period of time and is followed immediately by an opposite direction of current of a similar magnitude and duration. Multiphasic pulses comprise a plurality of pulsed waves in which current flows first in one direction, then in another direction, and so on, as required, at specified magnitudes and brief periods of time, in such a way that the charge associated with the total of all the plural pulses is balanced, whereby the net electrical charge delivered to the tissue over one multiphasic cycle is zero. These biphasic or multiphasic pulses are most often delivered in sequence to various sites, with the instantaneous magnitude at each site proportional to some measure of the amount of energy present in a particular frequency band of the acoustic waveform. The result is an impoverished (in terms of bandwidth and phase) but precisely controlled set of stimulus waveforms.

Both of the above stimulus waveform types—analog and biphasic/multiphasic—have been selected because they are relatively easy to produce and modulate electronically for real-time encoding of speech. Further, the waveform shape can readily be controlled so as to guarantee a charge-balanced alternating current at the electrodes, avoiding net direct current that is known to cause electrolytic damage to both electrodes and body tissues.

For purposes of the present application, the spatiotemporal manner in which either of the above two types of stimulus waveforms are applied to the cochlea of a patient is referred to as a "speech processing strategy." The spatial application of the stimulus waveforms is controlled by the type of electrode coupling, e.g., bipolar or monopolar, through which the stimuli are applied to various locations along the inside of the scala tympani duct of the spiral-shaped cochlea. The temporal application of the stimulation waveforms is derived by the timing of the stimuli. Traditionally, speech processing strategies have thus been classified as either: (1) a simultaneous strategy, or (2) a non-simultaneous, or sequential, strategy. Analog waveforms have traditionally been applied as part of a simultaneous strategy, relying on the more highly focused stimulation provided by bipolar coupling to produce an electrical pattern that will yield speech intelligibility. Short, non-simultaneous, biphasic or multiphasic pulses, on the other hand, are usually applied as part of a sequential speech processing strategy, relying on the highly precise sequence of stimulation pulses through monopolar coupling to produce the electrical pattern that yields speech intelligibility. In a typical sequential, or non-simultaneous, strategy, short biphasic pulses are applied in rapid succession (with little or no time overlap) in a specified pattern to each of multiple channels.

Not all patients benefit from the same speech processing strategy. That is, the complex biophysical phenomena associated with the electrical excitation of neurons and psychophysical phenomena regarding the interpretation of neural activity by the auditory nervous system suggest that the quality and intelligibility of speech percepts evoked by a cochlear prosthesis may be improved in a given patient by more specific manipulations of the electrical stimulus waveforms tailored to that patient.

When a cochlear prosthesis is first provided to a patient, including implanting any implantable components of the prosthesis into the patient (which implantable components typically include at least an electrode and a stimulator, and may also include, for fully implantable systems, a speech processor, a microphone and/or a rechargeable power source), it is necessary to initially "fit" or "adjust" the prosthesis. As used herein, it should be noted that the terms "fit", "adjust", "fitting" or "adjusting" relate to making electronic or software-programming changes to the prosthesis, as opposed to making physical or hardware changes, for the purpose of making the prosthesis better perform its intended function of helping the deaf patient to sense sound. Where more than one speech processing strategy is available within the prosthesis, selecting a speech processing strategy that is best suited for a particular patient thus becomes a key part of the "fitting" or "adjusting" process. Moreover, it should be recognized that the fitting or adjusting process will typically continue to occur at regular or as-needed maintenance/check-up intervals after the initial fitting. Thus, it is seen that where more than one speech processing strategy is available within the prosthesis, the patient, e.g., through the assistance of his or her physician or audiologist, may receive the benefit of, or at least try out during a trial period, one or more different speech processing strategies than was used initially.

Disadvantageously, not all cochlear prosthesis are capable of providing more than one speech processing strategy, or of providing both simultaneous and non-simultaneous speech processing strategies. Rather, most commercially-available cochlear prosthesis provide just one type of strategy (simultaneous or non-simultaneous), although some may offer, for example, multiple non-simultaneous strategies. Hence, with these one-type-strategy devices, the patient, and/or the physician/audiologist fitting the patient, has no, or only a very limited, ability to select a suitable speech processing strategy that is most effective for that patient. The Clarions cochlear stimulator, available from Advanced Bionics Corporation, of Sylmar California, is the only known commercially-available cochlear stimulator that allows the user to select either a simultaneous speech processing strategy or a non-simultaneous speech processing strategy as the technique for encoding the acoustic input signal into an electrical pattern that yields speech intelligibility. The Clarion® stimulator is described, inter alia, in U.S. Pat. No 5,603,726, which patent is incorporated herein by reference.

In U.S. Pat. No 5,626,629, incorporated herein by reference, there is disclosed one approach for fitting a Clarion®-type cochlear prosthesis, i.e., a multichannel cochlear prosthesis that offers more than one speech processing strategy, to a patient. While the techniques and tools taught in the '629 patent are very usefull and effective for many, if not most, fitting issues, an effective way to select an appropriate speech processing strategy for a particular patient is not addressed. Rather, the '629 patent assumes that one of a plurality of speech processing strategies will be selected, and that the fitting process will go forward based on that selected strategy. Hence, there remains a need for assisting the clinician, audiologist and/or physician in identifying which one(s) of several possible speech processing strategies are best suited for use within a given patient's multichannel cochlear prosthesis.

In U.S. Pat. No. 5,601,617, also incorporated herein by reference, there is disclosed a straightforward and understandable way of defining complex stimulation waveforms—both simultaneous and non-simultaneous waveforms—for use within a multichannel cochlear prosthesis, e.g., a Clarion® cochlear prosthesis. Disadvantageously, while the technique disclosed in the '617 patent is highly suitable for defining complex waveforms for use within a multichannel cochlear prosthesis, there remains a need for assisting the clinician, audiologist and/or physician in discovering which one(s) of several possible speech processing strategies—ranging from simultaneous analog strategies on one end of the spectrum to non-simultaneous pulsatile strategies on the other end of the spectrum—are best suited for use within the patient's multichannel cochlear prosthesis.

Where only sequential pulsatile speech processing strategies are used, it is known to specify the number of maxima N out of M possible sequential pulsatile channels that are to be used as part of the speech processing strategy. For example, where M sequential pulsatile channels are available, any number N of these M pulsatile channels, where N is thus an integer from 1 to M, may be selected as the number of maxima. Once the number of maxima is set by the selection process, the speech processing strategy then applies a suitable algorithm to determine which N of the M channels are to be stimulated per data frame. Typically, the N channels with the greatest input levels are selected for stimulation. See, e.g., Wilson, et al., "*Comparative Studies of Speech Processing Strategies For Cochlear Implants⇆*. 90*th Annual Meeting of American Laryngological, Rhinological and Otological Society, Inc.* (Denver, Colo. Apr. 1988). See also, U.S. Pat. Nos. 5,597,380; 5,271,397; and 5,095,904. Disadvantageously, while this "NofM" approach provides some selection ability with respect to sequential pulsatile channels, there remains a need to be able to use it in combination with simultaneous channels.

The present invention advantageously addresses the above and other needs.

SUMMARY OF THE INVENTION

The present invention provides a universal method and/or system whereby multiple speech processing strategies can be easily and quickly selected and modified for application to a patient having a multichannel implantable cochlear prosthesis. Such universal strategy selection method and/or system advantageously allows an audiologist or clinician to easily select and then test various speech processing strategies during the process of fitting such multichannel cochlear prosthesis. Advantageously, the selection of the different speech processing strategies is greatly facilitated by an easy-to-understand selection display, or selection screen, that provides a graphical representation of the stimulation waveforms associated with each channel of the selected strategy, a graphical representation of the electrode configuration pairing (also referred to herein as "electrode coupling", which may include multipolar virtual, bipolar, or monopolar coupling) used to apply the selected strategy, as well as a visual presentation of other selection criteria, such as the degree of simultaneity, the ratio or number of analog channels to pulsatile channels, the number of maxima, the firing order (i.e., sequence of stimulation of the various channels), the number of analysis channels, the number of stimulator channels, and the repetition rate per channel.

In accordance with one aspect of the invention, the selected speech processing strategy is selected from all of the different speech processing strategies made available within the particular multichannel cochlear prosthesis. Thus, where the multichannel cochlear prosthesis comprises a Clarion®-type cochlear prosthesis, which offers the capability of providing both simultaneous and non-simultaneous (sequential) speech processing strategies, the selected speech processing strategy may be made from all possible speech processing strategies—ranging from simultaneous analog strategies on one end of the spectrum to non-simultaneous pulsatile strategies on the other end of the spectrum. Where the multichannel cochlear prosthesis offers only different speech processing strategies of the same type, e.g., only non-simultaneous (sequential) pulsatile speech processing strategies, then the selected speech processing strategy may be made from all of the possible speech processing strategies ofthat type, e.g., a selection from all of the available sequential speech processing strategies. Advantageously, however, the selection of the speech processing strategy, from whatever group or collection of speech processing strategies is available within the multichannel cochlear prosthesis, is coupled with other useful information regarding the selection. Such other useful information may include, for example, an easy-to-understand selection display, a graphical representation of the stimulation waveforms associated with each channel of the selected strategy, a graphical representation of the electrode coupling, and/or a visual presentation of other selection criteria, such as degree of simultaneity, ratio or number of analog channels to pulsatile channels, number of maxima, firing order, number of analysis channels, number of stimulator channels, and/or repetition rate per channel.

The invention may thus be characterized as a universal strategy selector for use with a multichannel cochlear prosthesis. The multichannel cochlear prosthesis includes multiple stimulation channels through which a specific pattern of electrical stimulation, modulated by acoustic signals, and in accordance with a selected speech processing strategy, may be spatiotemporally applied to the cochlea in order to yield speech intelligibility. The universal strategy selector includes: (a) a processor, or equivalent; (b) a selector; and (c) a display.

The processor includes appropriate processing means coupled to the multichannel cochlear prosthesis for defining one of a plurality of speech processing strategies for use by the multichannel cochlear prosthesis. Typically, the processing means will be realized using a personal computer (PC), or a palm personal computer (PPC), programmed with appropriate software. In some embodiments of the invention, the multiplicity of speech processing strategies that may be selected includes at least one speech processing strategy that is a simultaneous speech processing strategy, such as a simultaneous analog sampler (SAS) strategy; and at least one other speech processing strategy that is a non-simultaneous speech processing strategy, such as a continuous interleaved sampler (CIS) strategy. The other speech processing strategies included within the multiplicity of strategies include one or more strategies whose temporal characteristics lie somewhere in between simultaneous or non-simultaneous, and whose stimulating waveform(s) comprises a hybrid combination of analog or pulsatile waveforms. In other embodiments of the invention, the multiplicity of speech processing strategies that may be selected include speech processing strategies of the same type, e.g., different types or variations of pulsatile sequential strategies.

The selector comprises a switch, pointer, or other selection means, for manually selecting one of the multiplicity of speech processing strategies as the selected speech processing strategy.

The display, which is controlled by the processing means, provides a graphical or visual representation that characterizes the selected speech processing strategy in terms of the degree of simultaneity of the applied stimuli, as evident from representative stimulation waveforms (e.g., pulse patterns) and electrode coupling (e.g., bipolar or monopolar) for each channel, as well as other stimulation parameters (e.g., number of maxima, number of channels, firing order, repetition rate, and the like).

In accordance with another aspect of the invention, the list of possible speech processing strategies from which a selection is made lists the available speech processing strategies in a logical or progressive order relative to a particular characteristic of the stimulation. For example, one characteristic of interest may be the degree of simultaneity of the strategy, in which case the list of available speech processing strategies would place a simultaneous speech processing strategy (e.g., SAS) on one end of the list, e.g., the top of the list, and would place a non-simultaneous strategy (e.g., CIS) on the other end of the list, e.g., the bottom of the list. Other characteristics of interest that may be used to order the list of possible speech processing strategies, particularly where only pulsatile speech processing strategies are available, may include, e.g., the number of maxima, firing order, pulse repetition rate, pulse width, or the like.

In accordance with still another aspect of the invention, the number of maxima associated with pulsatile stimulation strategies may be selected along with the selection of the speech processing strategy, which speech processing strategies include both simultaneous and non-simultaneous strategies. For example, where the selected speech processing strategy includes Mpulsatile channels out of L total channels, any number N of these M pulsatile channels, where N is thus an integer from 1 to M, may be selected as the number of maxima (referred to herein as "NofM"). Once the number of maxima is set by the selection process, the processor that defines the speech processing strategy then applies an appropriate algorithm to determine which N of the M channels are stimulated per data frame. Typically, the N channels with the greatest input levels may be selected for stimulation.

In accordance with yet an additional aspect of the invention, the graphical representation of the electrode coupling is presented by displaying a drawing of the electrode array, with each electrode contact of the array being included in the drawing (with the exception of a common return electrode, if used), and with shading or distinctive coloring being used in the display to clearly depict which electrode contacts are paired together for stimulation. Advantageously, such electrode array drawing, presented on the selection screen along side the other selection criteria, thus unequivocally conveys to the individual performing the selection process exactly what type of electrode coupling will result from a given selection.

It is thus a feature of the present invention to provide a system whereby a patient or audiologist or other medical personnel can readily select and test an appropriate speech processing strategy for effective use within a patient's multichannel cochlear prosthesis.

It is a further feature of the present invention to provide a fitting method or process that allows an audiologist or clinician to select and test multiple speech processing strategies—ranging from simultaneous analog strategies to non-simultaneous pulsatile strategies—within an implanted multichannel cochlear prosthesis over the course of a relatively short fitting session.

It is an additional feature of the invention to provide an easy-to-use speech processing strategy selection process for use with a multichannel implantable cochlear stimulator that unequivocally and understandably coneys to the individual performing the selection exactly what type of speech processing strategy is associated with each possible strategy selection. In this regard, it is a feature of the invention that information defining the speech processing strategy is conveyed to characterize the speech processing strategy in terms of its degree of simultaneity, number of analog/pulsatile channels, pulse pattern, number of maxima, electrode coupling, firing order, number of channels, envelope detection/channel, repetition rate, or the like.

BRIEF DESCRIPTION OF THE DRAWINGS

The above and other aspects, features and advantages of the present invention will be more apparent from the following more particular description thereof, presented in conjunction with the following drawings wherein:

FIG. 3C presents a preferred frequency map for the filter bank used within the speech processor for two different speech processing strategies;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is to be emphasized that while the following description of a presently-preferred embodiment of the invention relates to a multichannel cochlear implant system (also referred to as a cochlear stimulation system) that has the capability of selectively generating both simultaneous and non-simultaneous (i.e., sequential) speech processing strategies, the invention set forth in the claims is not intended to be so limited. Rather, any multichannel cochlear implant system that is capable of generating a plurality of speech processing strategies, e.g., a plurality of pulsatile, non-simultaneous strategies, or a plurality of simultaneous strategies, one of which must be selected during a "fitting" operation, may benefit from application of the present invention.

Additionally, it should be noted that while the following description describes the invention in terms of the Clarion® cochlear implant system, which cochlear implant system is commercially available from Advanced Bionics Corporation, of Sylmar, Calif., the invention is not limited to the Clarion® cochlear implant system, per se. Rather, the invention is directed to a particular system, or method, of allowing one of a plurality of speech processing strategies to be selected during a fitting session. The Clarion® system is referenced and described herein as just one example of how the best mode of the invention may be implemented. Hence, because the Clarion® system is not the subject of the invention, per se, many of the details associated with the Clarion® implantable cochlear stimulator (ICS) and the entire Clarion® implant system, including its speech processor and headpiece, are not presented herein, but may be found elsewhere, or are known in the art. For example, the Clarion® implantable cochlear stimulator (ICS) is fully described, inter alia, in U.S. Pat. No. 5,603,726, previously incorporated herein by reference. Detailed information regarding a suitable fitting procedure, as well as software fitting tools, that may be used with the Clarion® implant system may be found in the following document: "*SCLIN 98 for Windows Device Fitting Manual*" (Advanced Bionics Corporation, Sylmar, Calif., 1998). Such Device Fitting Manual was part of U.S. Provisional Patent Application Serial No. 60/087,656, filed 06/02/1998, and is incorporated herein by reference. It should also be pointed out that such Device Fitting Manual is now a publicly-available document.

Figure 1:
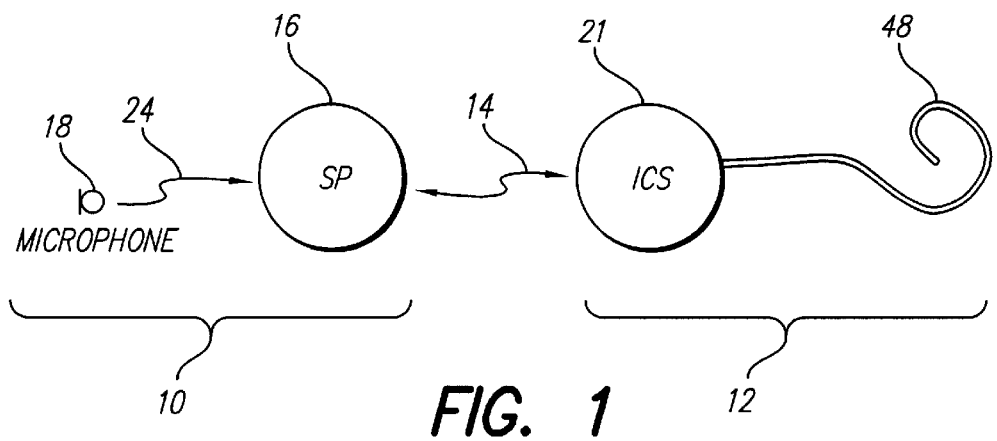
FIG. 1 shows a generalized block diagram of a cochlear stimulation system, including a microphone, a speech processor (SP), an implantable cochlear stimulator (ICS) and an electrode array.

Turning then to FIG. 1, the present invention will be described. As seen in FIG. 1, a cochlear stimulation system is shown that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 "Cochlear Electrode Array With Electrode Contacts on Medial Side", also incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are linked together electronically through a suitable communications link 14 that allows power and control signals to be sent from the SP 16 to the ICS 21, and that (in some embodiments) allows data and status signals to be sent from the ICS 21 to the SP 16. The details of such communication link 14 are not important for purposes of the present invention. In some embodiments, i.e., where the ICS 21 and electrode array 48 are implanted within the patient, and the SP 16 and microphone 18 are carried externally (non-implanted) by the patient, the link 14 may be realized by an antenna coil in the ICS and an external antenna coil coupled to the SP. In such embodiment, i.e., when the ICS has been implanted, the external antenna is positioned so as to be aligned over the location where the ICS is implanted, allowing such coils to be inductively coupled to each other, thereby allowing information (e.g., the magnitude and polarity of a stimulation current) and power to be transmitted from the speech processor 16 to the ICS 21. In other embodiments, i.e., where both the SP 16 and the ICS 21 are implanted within the patient, the link 14 may be a direct wired connection, or other suitable link.

The microphone 18 senses acoustic signals and converts such sensed signals to corresponding electrical signals. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS.

It is common in the cochlear stimulator art to condition the magnitude and polarity of the stimulation current applied to the implanted electrodes of the electrode array 48 in accordance with a specified speech stimulation strategy. Such speech stimulation strategy involves defining a pattern of stimulation waveforms that are to be applied to the electrodes as controlled electrical currents. If multiple electrode pairs exist, as is the case with a multichannel cochlear stimulator of the type used with the present invention, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one wherein stimulation currents, either analog or pulsatile, are applied to the electrodes of two or more channels, but not necessarily all of the channels, at the same time. Examples of each type are given below.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy, explained more fully below.

Current pulses applied in pulsatile stimulation patterns are generally biphasic pulses applied to the electrodes of each channel. The biphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multi-channel cochlear stimulators of the type used with the present invention, it is common to sample the acoustic signal at a rapid rate, and apply a biphasic stimulation pulse in sequence (i.e., non-simultaneously) to each of the pairs of electrodes of each channel in accordance with a specified pattern and cycle time, with the magnitude of the stimulation current being a function of information contained within the sensed acoustic signal at a given (e.g., the most recent) sample time. An example of such sequential, non-simultaneous stimulation pattern is a continuous interleaved sampler (CIS) strategy, as explained more fully below.

It is important to recognize that in between the two extremes of fully simultaneous stimulation patterns (wherein analog stimulation currents are continuously applied to all channels, e.g., using the SAS strategy) and non-simultaneous pulsatile patterns (wherein biphasic pules are applied in a specified sequence to all channels without time overlap, e.g., using the CIS strategy), there are a great number of other stimulation patterns that may be formulated. Such other simulation patterns may prove more efficacious for a given patient than either of the SAS or CIS strategies. Thus, a primary purpose of the present invention is to provide a method or process whereby these "other" stimulation patterns may be identified and tested on a given patient in order to determine their effectiveness, thereby aiding the clinician or audiologist (or other medical personnel) to fit the patient (i.e., program the patient's cochlear stimulator) with the most effective combination of stimuli parameters or speech processing strategy.

It is also important to realize that not all cochlear stimulation systems are capable of producing all types of stimulation strategies. Thus, while the present invention may find primary applicability for use with cochlear stimulation systems having multiple independent current sources that can be used to independently generate the electrical stimuli applied through the electrodes of the various channels (thereby offering the capability of being programmed to provide a simultaneous, non-simultaneous, or hybrid (i.e, a combination of simultaneous and non-simultaneous) electrical stimulation patterns), the present invention may also be used with cochlear stimulation systems of lesser capability.

In general, heretofore, all known cochlear stimulation systems have been severely limited in their ability to specify more than one or two stimulation patterns for use with the implantable stimulator. Moreover, what patterns have been available have been limited to very simple stimulation waveforms, e.g., non-simultaneous patterns involving sequencing through each electrode pair in a fixed sequence with simple biphasic pulses of varying amplitude, or sequencing through each electrode pair in a fixed sequence with simple biphasic pulses of varying width. Except for the Clarion® cochlear stimulator system, there are no cochlear stimulation systems known to applicants that permit complex stimulation waveforms to be individually tailored for each stimulation site (where each "stimulation site" corresponds to a selected electrode or electrode group). The present invention advantageously overcomes this limitation, and allows a speech processing strategy to be readily selected and understood even when the cochlear stimulator provides an almost infinite variety of complex stimulation waveforms that can be easily specified and thereafter generated by the implantable stimulator. Such flexibility in defining or specifying the stimulation patterns thus allows the audiologist or other medical personnel fitting the implantable unit, to readily select the stimulation patterns and waveforms, i.e., speech processing strategies, that are most beneficial for a particular patient.

Figure 2A:
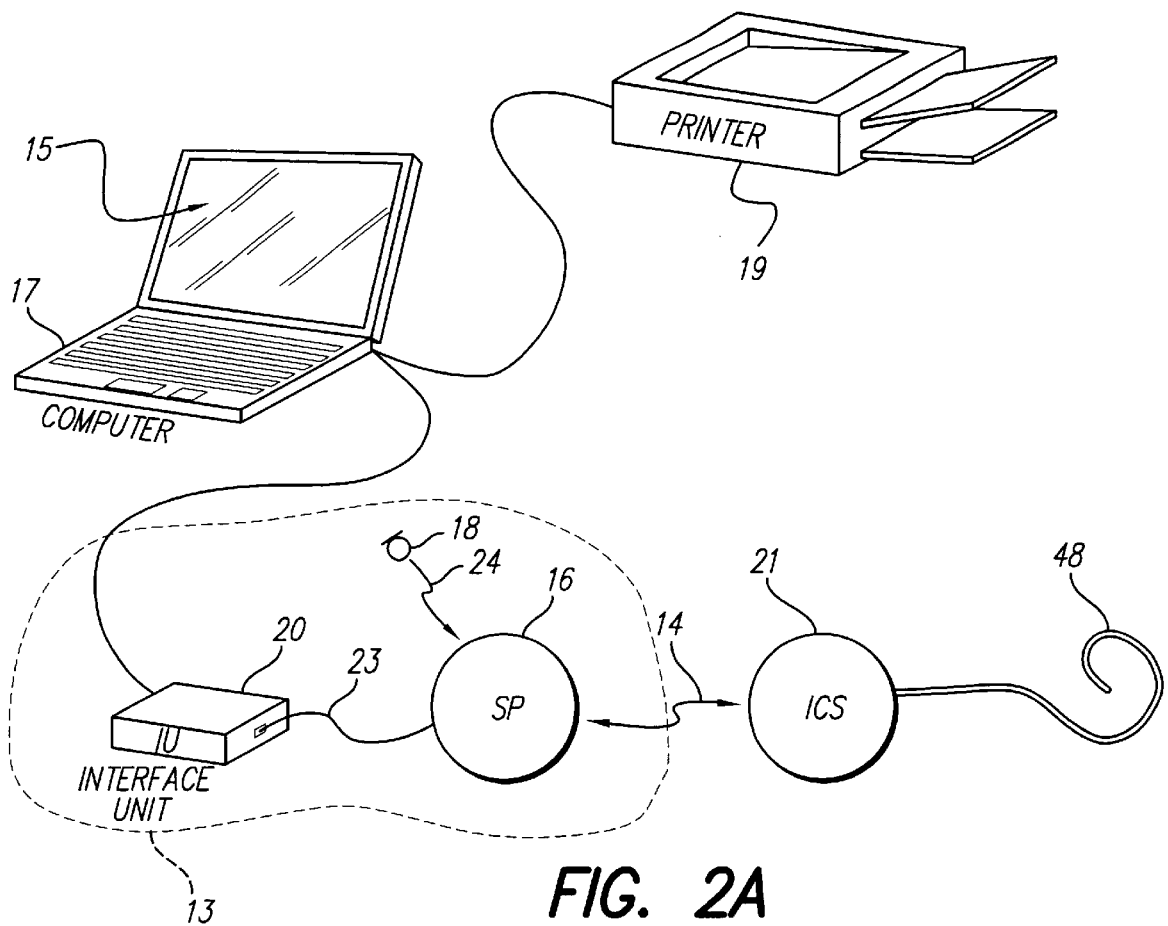
FIG. 2A depicts the elements of a typical fitting system used with the cochlear stimulation system of FIG. 1.

Referring next to FIG. 2A, a block diagram of the basic components used to fit a given patient with a cochlear implant system is shown. As seen in FIG. 2A, the implant system is as shown in FIG. 1, and includes the SP 16 linked to an ICS 21 with electrode array 48. A microphone 18 is also linked to the SP 16 through a suitable communication link 24. A laptop computer 17, or other type of computer, or equivalent device, is coupled to the speech processor 16 through an interface unit (IU) 20, or equivalent device. The type of linkage 23 established between the IU 20 and the SP 16 will vary depending upon whether the SP 16 is implanted or not. Any suitable communications link 23 may be used, as is known in the art, and thus the details of the link 23 are not important for purposes of the present invention. It should be noted that for some applications, the IU 20 may be included within the computer 17 (e.g., as a communications interface already present within the computer, e.g., a serial port, or other built-in port, e.g., an IR port).

The computer 17, with or without the IU 20, provides input signals to the SP 16 that simulate acoustical signals sensed by the microphone 18 and/or provide command signals to the SP 16. In some instances, e.g., when testing the patient's threshold levels, the signals generated by the computer 17 replace the signals normally sensed through the microphone 18. In other instances, e.g., when testing the patient's ability to comprehend speech, the signals generated by the computer 17 provide command signals that supplement the signals sensed through the microphone 18.

The laptop computer 17 (or equivalent device) provides a display screen 15 on which selection screens, stimulation templates and other information may be displayed and defined. Such computer 17 thus provides a very simple way for the audiologist or other medical personnel, or even the patient, to easily select and/or specify a particular pattern of stimulation parameters that may be thereafter used, even if for just a short testing period, regardless of whether such stimulation pattern is simple or complex. Also shown in FIG. 2A is a printer 19 which may be connected to the computer 17, if desired, in order to allow a record of the selection criteria, stimulation templates and pattern(s) that have been selected and/or specified to be printed.

Figure 2B:
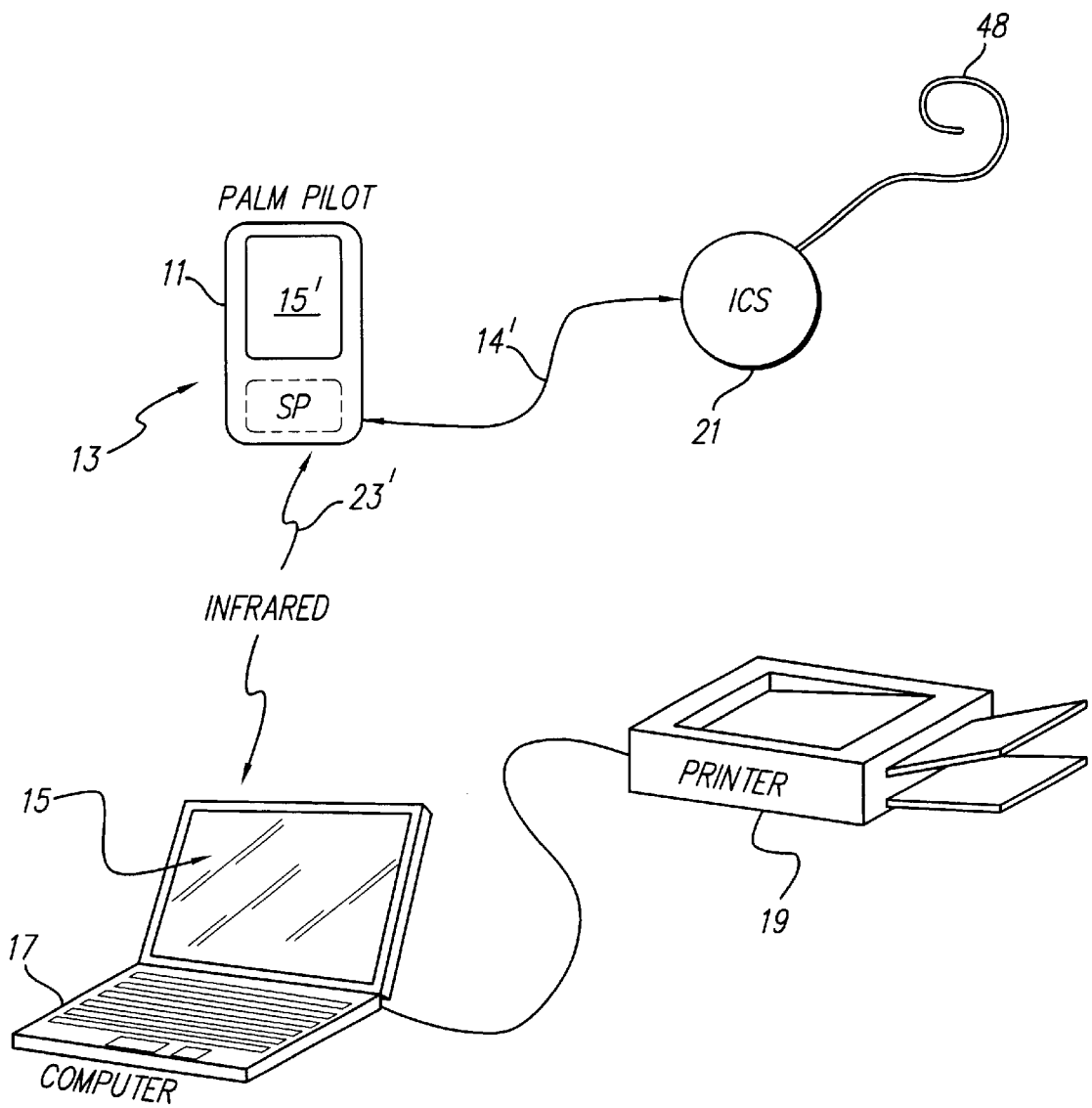
FIG. 2B depicts the elements of an alternate fitting system.

FIG. 2B illustrates an alternative fitting system that may also be used with the invention. In FIG. 2B, the ICS 21 is linked to a speech processor configured or emulated within a palm personal computer (PPC) 11, such as a Palm Pilot, or equivalent processor, commercially available, e.g., from Hewlett Packard Such PPC 11 includes its own display screen 15' on which some graphical and textual information may be displayed. In use, the PPC 11 is linked, e.g., through an infrared link 23', to another computer, 17, as necessary. Typically, the functions of the SP and related devices are stored in a flashcard (a removable memory card that may be loaded into the PPC 11), thereby enabling the PPC 11 to perform the same functions of those elements encircled by the dotted line 13 in FIG. 2A. . The PPC 11 is coupled to the ICS 21 through a suitable data/power communications link 14'.

Figure 3A:
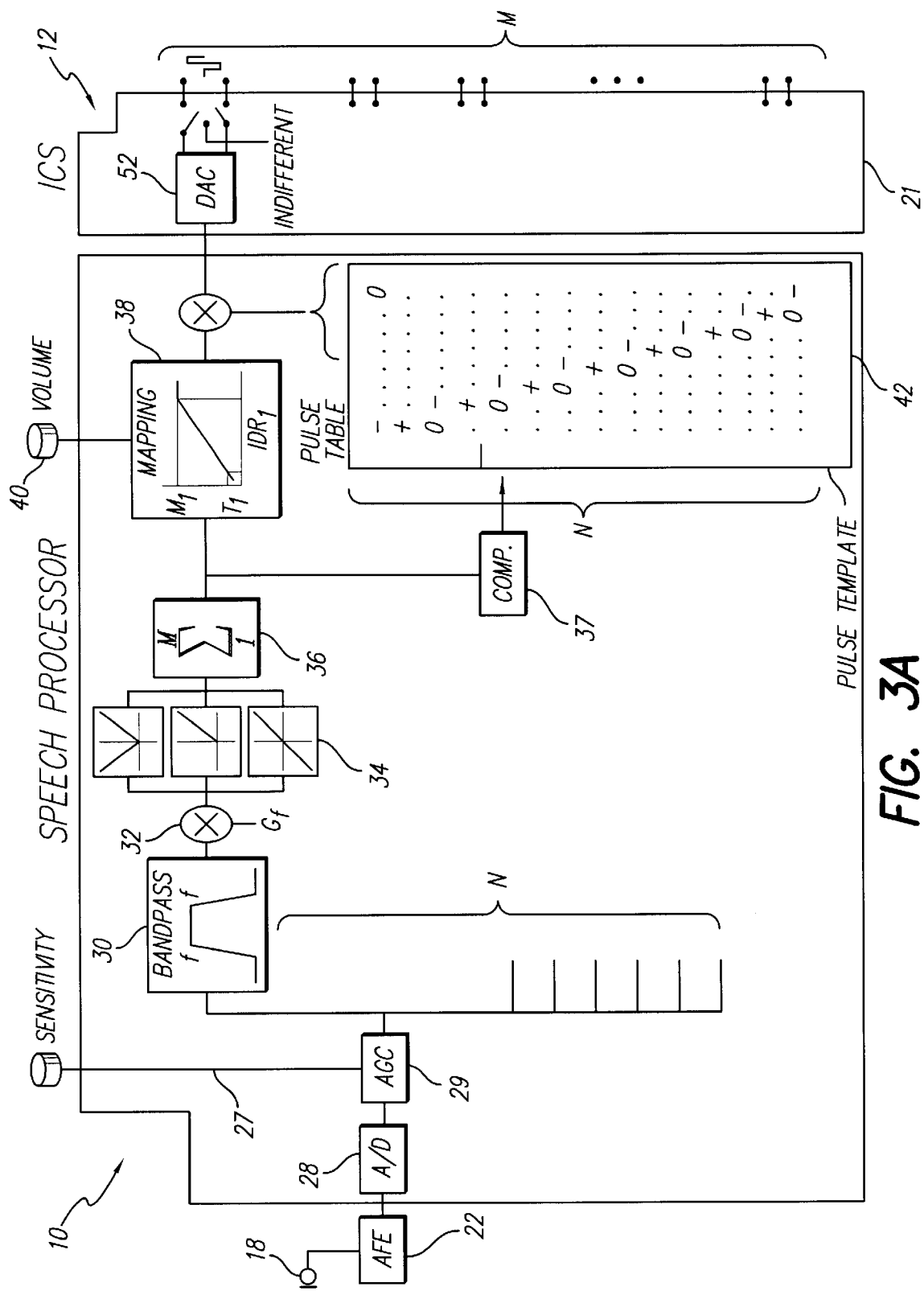
FIG. 3A is a functional block diagram of one channel of the speech processor and ICS portions of a multichannel cochlear stimulation system.

Turning next to FIG. 3A, a partial functional block diagram of the SP 16 and the ICS 21 of the system of FIG. 1 is shown. It is to be emphasized that what is shown in FIG. 3A depicts the functions that are carried out by either the SP 16 or the ICS 21. The actual electronic circuitry that is used to carry out these functions is not critical to the present invention, although a representation of circuitry that may be used for this function is shown in the previously cited patents and patent applications. It should also be pointed out that the particular functions shown in FIG. 3A are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

In FIG. 3A, it is seen that the speech processing portion 10 includes a microphone 18 that senses acoustical information and converts it to electrical signals. These signals are then amplified in audio front-end (AFE) circuitry 22. The amplified audio signal is then converted to a digital signal by analog-to-digital (A/D) converter 28. The resulting digital signal is then subjected to automatic gain control (AGC) processing using a suitable AGC algorithm 29. The function of the AGC algorithm is to compress the dynamic range of the speech signals so as to provide a more consistent overall level of stimulus to the electrodes, as well as to equalize the level between close and more distant speakers in a given area, e.g., within a room. The AGC algorithm 29 operates by measuring the volume level of the signal and using the measurement result to control a variable gain stage. The gain is controlled by two loops, where the lowest control voltage of the two loops is selected. One loop performs syllabic compression by responding slowly to sounds above about 55 dB SPL, the second loop performs as a compression amplifier by responding quickly to sounds over about 67 dB SPL. [For a discussion of sound levels, and a definition of dB SPL, see "Moore, Brian C. J., "An Introduction to the Psychology of Hearing", Fourth Edition, pp. 9–12 (Academic Press 1997).] A sensitivity control 27 is coupled to the AGC circuit 29. The sensitivity control 27 may be either a dial or remote control, preferably a remote control, and may vary either front-end gain and/or AGC parameters.

As seen in FIG. 3A, after processing by the AGC algorithm 29, the signal is processed in one of a multiplicity of digital signal processing channels. For example, eight separate analysis channels may be used, each responding to a different frequency content of the sensed acoustical signal.

In other words, the incoming signal is divided into a multiplicity of N frequency channels, as defined by a bank of respective bandpass or other filters 30. Note that the lowest frequency filter may be a lowpass filter, and the highest frequency filter may be a high-pass filter.

Figure 3B:
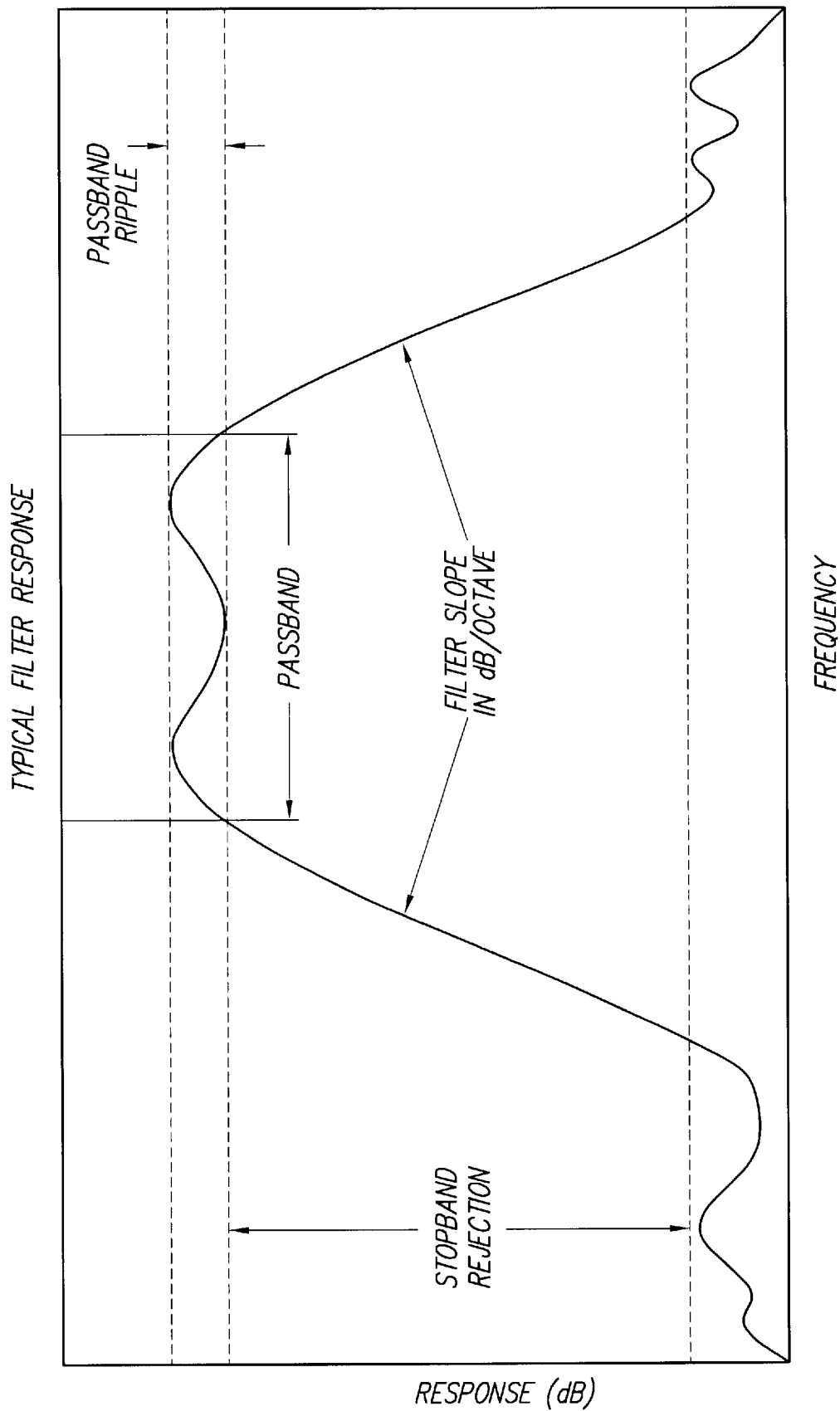
FIG. 3B depicts a typical filter response of the bandpass filter used in most of the channels of the speech processor of a multichannel cochlear stimulation system.

Typical characteristics of the passband filters are illustrated as shown in FIG. 3B. All of the filters have a maximum pass band ripple of 3 dB, a stop band rejection of at least 50 dB, a filter slope of 39 dB/octave, and internal filter noise of at least 50 dB below the signal.

The gain of each filter is equal for all channels by default, but may be modified by a user in ±10 dB increments, if desired. In FIG. 3A, the gain associated with the filter stage is functionally illustrated as a multiplication element 32, driven by the gain of the filter $G_f$. In an actual hardware implementation, as is known to those of skill in the art, the filtering and gain functions are typically carried out in a common amplifier/filter stage. In an actual software implementation, as is also known in the art, the filtering and gain functions may be performed sequentially, as shown in FIG. 3A.

One type of frequency map for the filters is shown in FIG. 3C. As seen in FIG. 3C, a slightly different frequency map is used by default for SAS than is used for CIS. Still other frequency maps may be readily used and new ones defined, as required, for all speech processing strategies that may be selected through use of the present invention.

Returning back to FIG. 3A, it is seen that after the received signal is filtered, and amplified, it is subjected to a rectification stage 34. Standard analog strategies bypass this stage. Strategies that utilize charge balanced pulses, or use envelopes (e.g., speech envelopes), either use full-wave rectification (absolute value) or half-wave rectification. Full-wave rectification provides a more spectrally pure signal than half-wave, but the spiral ganglion nerve cells, under certain conditions, seem to perform a type of half-wave rectification.

After rectification, the signal is further processed in an integration stage 36. Integration is used to perform the function of envelope detection, i.e., to detect the amount of energy present in the signal. A simple integrator is used for the preferred envelope detection. Although such may not be an optimal implementation, it easily adapts to changing repetition rates and requires no multipliers. The resulting spectrum is a sinx/x function.

It should be noted that non-simultaneous stimulation has the effect of reducing the repetition rate, where the slow down is proportional to the number of channels and the minimum pulse width. Thus, when non-simultaneous stimulation is used, several mechanisms may be used to raise the rate. A first is to select at the beginning of each repetition cycle (where the repetition cycle may be considered as the beginning of the data frame, see FIG. 4) the channels with the highest energy, and then only stimulate the corresponding electrodes. This is referred to as "NofM," orNumber of Maxima, strategy, and (at least with respect to pulsatile channels) is a prior art strategy that has been referenced previously. A second is to reduce the number of total channels. A third is to reduce the pulse width. A fourth is to stimulate at least some electrodes simultaneously, this being more appropriate for non-focused electrodes.

As practiced by the present invention, NofM is implemented on pulsatile channels in combination with simultaneous stimulation, e.g., pulsatile simultaneous stimulation, by either: (1) selecting a threshold where stimulation takes place, which may result in a variable frame rate; or (2) setting the number of electrodes (e.g., 6 of 8) that will be stimulated during each repetition cycle, and then determining which of the N channels have the highest energy, and then selecting only those N channels during the repetition cycle. These implementation techniques rely on some type of energy detector, e.g., an envelope detector, and a comparator to compare the detected energy to a suitable threshold.

Thus, referring to FIG. 3A again, it is seen that after integration (in processing block 36), or energy detection, the signal is processed in two parallel paths. In a first signal processing path after integration, the signal is applied to a comparator 37. The comparator is used to implement an NofM strategy and compares the detected energy to set thresholds. If the threshold is exceeded, then that information is forwarded to a pulse or stimulation template 42. The function of the pulse template 42 is explained below, but basically it defines the particular stimulus patterns that are applied to the patient through the ICS.

In a second signal processing path after integration, the signal is compressed, sample for sample, according to a specific compression rule, in a compression stage 38. The following logarithmic rule represents a preferred rule:

1. if the input <=0, the output is set to zero
2. if the input >MCL, then the output is set to M, where MCL is a most comfortable level for the user (patient) of the cochlear stimulator.
3. if 0<the input<MCL, then the output=A*log(input)+K where "A" and "K" are constants that are determined by the results of the clinicians tests. For example, "A" and "K" may be determined for each patient by solving simultaneously the following equations:

$$M=A*\log(MCL)+K$$

$$T=A*\log(IDR)+K$$

where:

$$A=(M-T)/[\log(MCL)-\log(IDR)]$$

$$K=T-\{(M-T)\log(IDR)/[\log(MCL)-\log(IDR)]\}$$

Figure 3D:
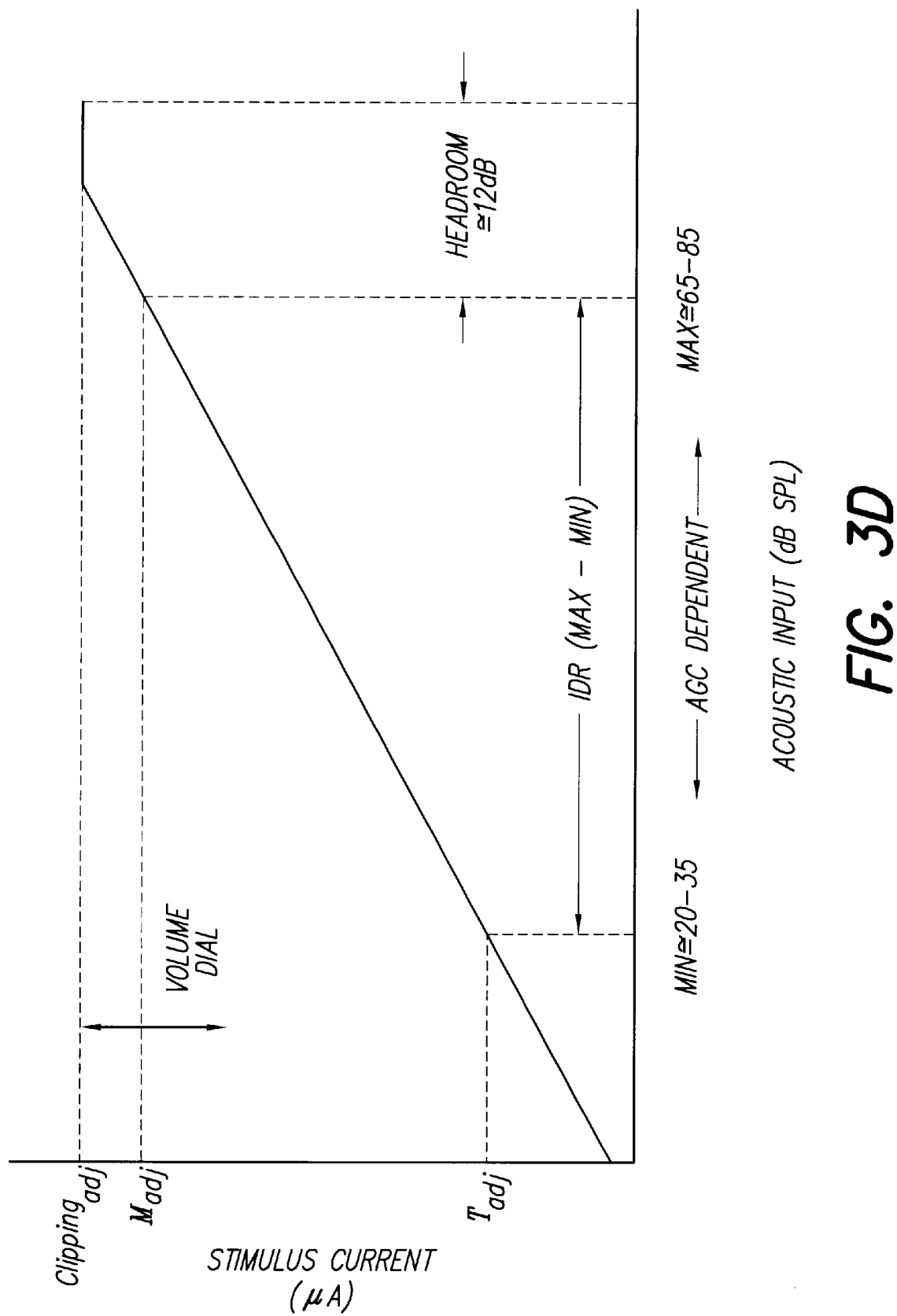
FIG. 3D shows a preferred channel compression transfer function used within each channel of the speech processor of a multichannel cochlear stimulation system.

A plot of the above logarithmic mapping function against linear sound pressure and stimulus current is shown in FIG. 3D.

Note: here, the T and M levels, and the MCL, are parameters determined during the early phases of a fitting session, and are described more fully in the patents and documents previously referenced)

Effectively, the above procedure sets or biases the input signal in any given channel to be compressed and mapped between the patient's T and M levels, and/or between 0.5 and M levels, where the T and M levels are as defined above. In the equations above, the maximum input is determined by the level of the signal into this transform. Generally speaking, the level is set so that a male conversational voice at 18" will produce a signal at the acoustic MCL (most comfortable level). Input dynamic range (IDR) is typically set to the noise floor of the electronic system or a little higher to rid the user of higher levels of background noise in a particular environment. The range between MCL and IDR is selectable between 20 to 80 dB below MCL, which represents the dynamic range of the post A/D processing.

Turning back to FIG. 3A, it is seen that a volume function 40 is also used in conjunction with the compression function 38. In operation, after compression, all of the amplitude signals are linearly scaled by a factor, which is controlled by the volume control 40. The volume control 40 has the effect of shifting the M stimulation levels up or down by a percentage of the electrical dynamic range. The default settings of the upper and lower volume range are +100% and −100%. All of the Ms are scaled by the same factor, a percentage of each channel's electrical dynamic range as shown in the following equation:

$$M_{new}=M_{initial}+\text{scaling factor}*(M_{initial}-T)$$

Since the preferred ICS DAC 52 is exponential in nature, a second log lookup may be performed in order to linearize the output.

After the signal has been appropriately compressed, an appropriate stimulation template 42 is applied to the signal in order to generate the control signals that are sent to the ICS 21 so that the desired stimulation pulses may be applied to the patient through the electrode array 48 (FIGS. 1 and 2). The use of the stimulation template to provide a wide range of different and varied speech stimulation strategies is the subject of U.S. Pat. No. 5,601,617, previously incorporated herein by reference. Only a brief summary of how such templates are defined and used will be presented herein. For additional details, the reader should refer to the '617 patent.

Before describing a brief summary of the pulse or stimulation template 42, however, it will be helpful to consider an important, but frequently overlooked, feature of the present invention. The system as configured in FIG. 3A provides a multiplicity of channels, N, wherein the incoming signal is analyzed. The information contained in these N "analysis channels" is then appropriately encoded, e.g., using the pulse template table 42, in order to control the actual stimulus patterns that will be applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., M stimulus channels, exist through which individual electrical stimuli may be applied at M different stimulation sites within the patient's cochlea.

Figure 3E:
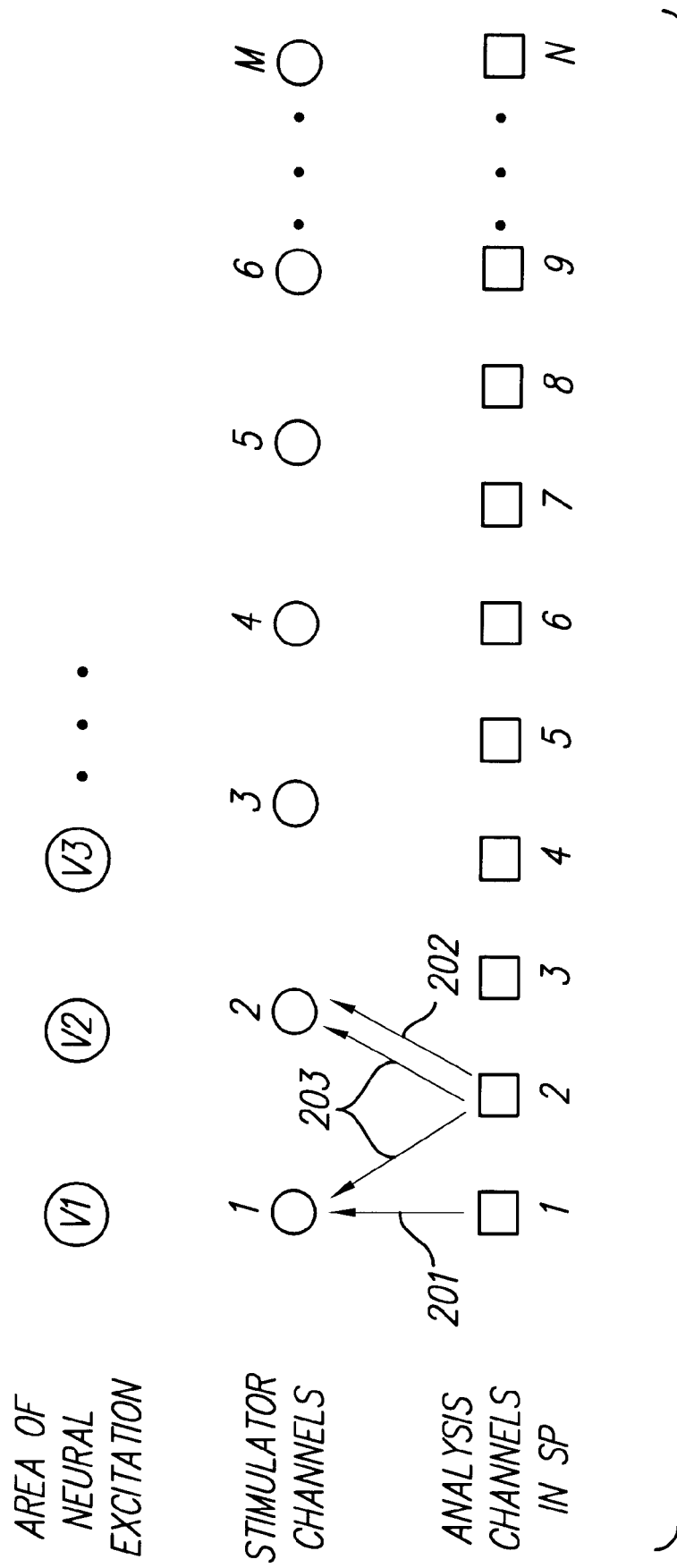
FIG. 3E shows how multiple analysis channels in the speech processor may be mapped with multiple stimulator channels in the cochlear stimulator in order to provide multiple neural excitation sites.

The above-described concept—of having N analysis channels controlling M stimulation channels—is schematically illustrated in FIG. 3E. While it is common to use a one-to-one mapping scheme between the analysis channels and the stimulus channels, wherein N=M and the signal analyzed in the first analysis channel is mapped to produce a stimulation current at the first stimulation channel, and so on, for each of the N and M channels, it is not necessary to do so. Rather, in some instances, a different mapping scheme may prove beneficial to the patient. For example, as depicted in FIG. 3E, assume that N is not equal to M (N, for example could be at least 20 or as high as 32, while M may be no greater than sixteen, e.g., 8 to 16). The signal resulting from analysis in the first analysis channel of the speech processor may be mapped to the first stimulation channel via a first map link 201 (FIG. 3E), resulting in a first stimulation site (or first area of neural excitation) V1. Similarly, the signal resulting from analysis in the second analysis channel of the SP may be mapped to the second stimulation channel via a second map link 202, resulting in a second stimulation site V3. Also, as seen in FIG. 3E, the signal resulting from analysis in the second analysis channel may be jointly mapped to the first and second stimulation channels via a joint map link 203. This joint link 203 would result in a stimulation site V2 that is somewhere in between the V1 and V3 stimulation sites. The V2 site is sometimes referred to as a virtual stimulation site. Advantageously, this possibility of using different mapping schemes between "N" SP analysis channels and "M" ICS stimulation channels to thereby produce a large number of virtual and other stimulation sites provides a great deal of flexibility with respect to positioning the neural excitation areas in a location that proves most beneficial to the patient.

Figure 4:
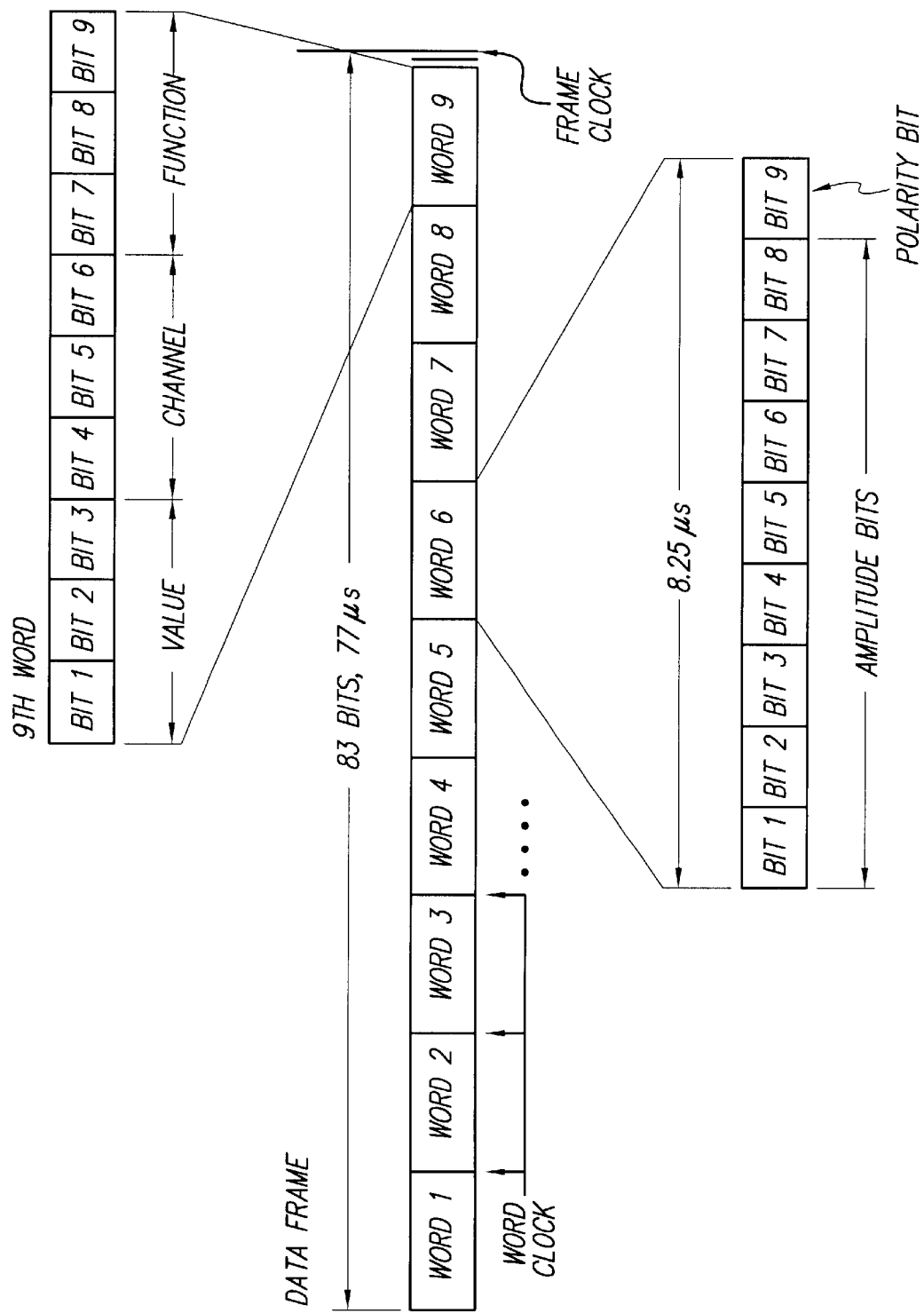
FIG. 4 shows the makeup of a data frame that may be used, in one embodiment of the invention, to transfer information from an external speech processor (SP) to an implantable cochlear stimulator (ICS)

Next, to further explain how the stimulation template 42 (FIG. 3A) defines a particular speech processing strategy, reference is made to FIG. 4, where there is shown the makeup of a typical data frame that may be used with a representative cochlear stimulation system, e.g., the CLARION® cochlear stimulator described in the '726 patent, previously incorporated herein by reference. The use of such a data frame is necessary due to the fact that multiple channels of stimulation information are needed by the ICS 21, yet (for the embodiment shown in the '726 patent, as well as most embodiments) there is only a single telecommunications channel 14 (FIGS. 1 or 2) through which information may be transferred to the ICS. In other words, use of the data frame shown in FIG. 4 allows parallel data channels to be temporarily reformatted into a serial data channel to facilitate transmission of the information to the ICS. Such serial transmission is needed when the transmission is through a single serial data channel realized via a transcutaneous link from an external speech processor to an implanted cochlear stimulator. But, even when the speech processor is implanted, e.g., in a separate case or housing than is the cochlear stimulator, as taught e.g., in U.S. patent application Ser. No. 09/126,615, filed Jul. 31, 1998, incorporated herein by reference, the link between the implanted speech processor and the implanted cochlear stimulator may still need to be a serial link in order to minimize the number of interconnections between the two implanted devices. Thus, more often than not, it is necessary to use a serial data channel somewhere in the system even though parallel data channels are used to process sensed data and to stimulate the patient.

As seen in FIG. 4, a representative data frame is made up of 9 nine-bit words, plus a parity bit and an end-of-frame bit, or a total of 83 bits. The clock rate is such that the overall duration of a complete data frame is about 77 $\mu$sec.

The first eight words in the data frame are data words, and each contains amplitude bits (the first eight bits) and a polarity bit. Each data word corresponds to the stimulation information for a given channel. The last word of the data frame, or the ninth word, is a control word. Such word is used to control and/or set various functions within the ICS, e.g., the electrode configuration (bipolar or monopolar) that the ICS will use. The general format of the control word is also shown in FIG. 4.

Figure 5:
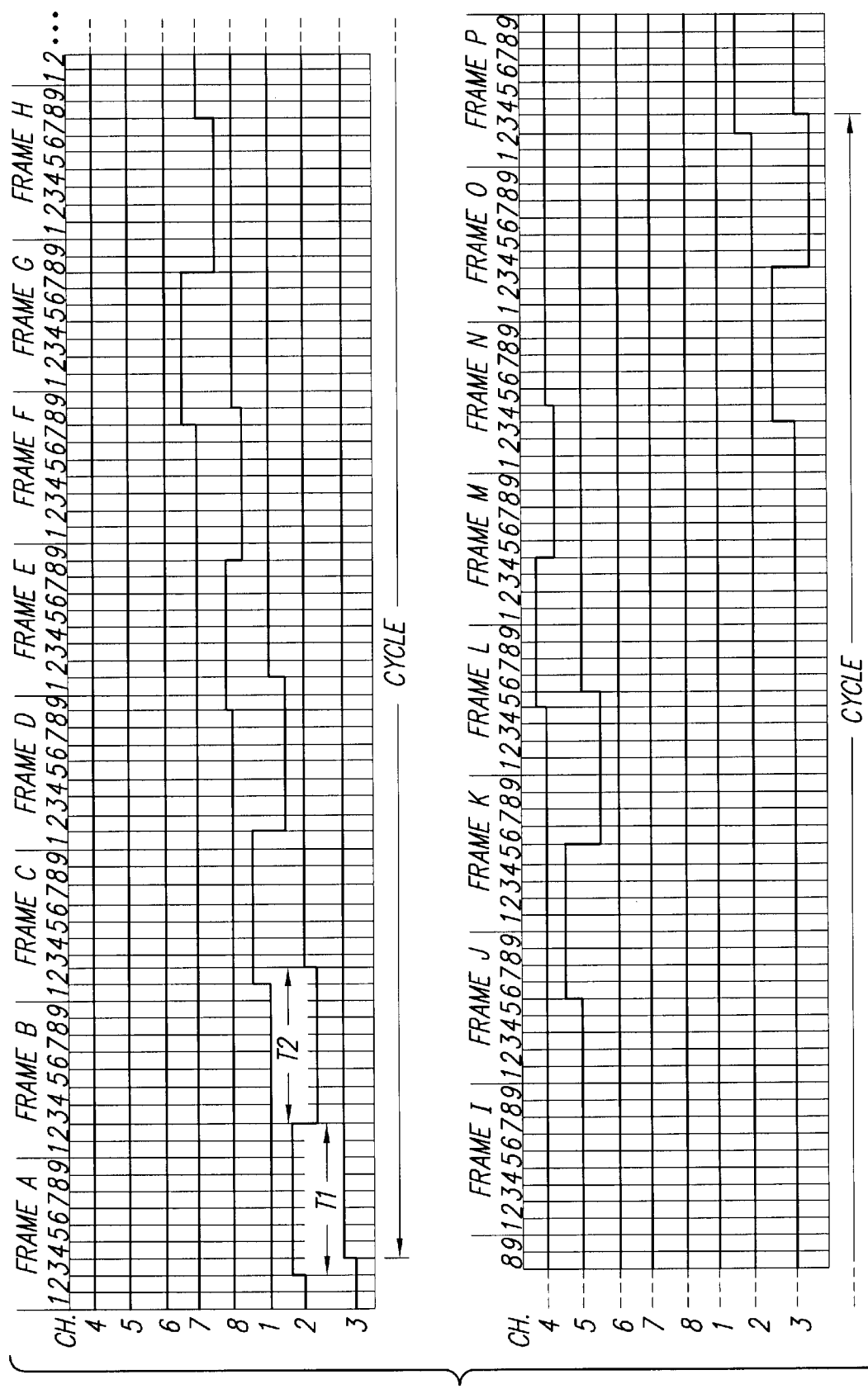
FIG. 5 illustrates how multiple data frames may be used with the cochlear stimulation system in order to achieve a desired stimulation pattern that repeats itself in cycles.

FIG. 5 illustrates how multiple data frames may be used with the system of FIG. 3 to achieve a desired stimulation pattern that repeats itself in cycles. The particular stimulation pattern shown in FIG. 5 approximates a simple CIS strategy because, for the most part, only one electrode pair (channel) is stimulated with a biphasic pulse at any given time, although there is a slight overlap in time when two electrode pairs are stimulated at the same time. To understand FIG. 5, it is important to recognize that the data word in each data frame specifies the amplitude and polarity for the stimulation current of the corresponding channel. Such amplitude and polarity, once set by a data word, remains unchanged until a new data word, in a new data frame, is received to make a change. Thus, to produce a biphasic stimulation pulse, it is necessary to specify an amplitude and polarity for the channel in a first data frame, specify the amplitude and opposite polarity in a second data frame, and finally, specify a zero amplitude in a third data frame. If a CIS strategy is employed, as approximated in FIG. 5, then each channel is maintained at a zero amplitude until such time in the cycle as it is that channel's turn to be stimulated in the specified sequence.

As shown in FIG. 5, for example, the specified sequence (or firing order) comprises (starting at the left of the figure) stimulating the electrode pair of channel 2, then channel 1, then channel 8, then channel 7, then channel 6, then channel 5, then channel 4, and then channel 3. In a first data frame, Frame A, a positive stimulation current is applied to the electrodes of channel 2. The magnitude of this stimulation current is a function of the sensed acoustic signal falling within the frequency band corresponding to channel 2, and as otherwise processed by the speech processor 16. Note that during data Frame A, not only is channel 2 stimulated, but the stimulation current already present in channel 3 is turned off. This process continues, as shown, with each phase of the biphasic pulse lasting for a time equal to the length of a data frame, and with the complete stimulation cycle requiring 16 data frames.

Still referring to FIG. 5, the numbers 1–9 included for each data frame correspond to the nine data words present in each data frame. Thus, when a change is included in the first word of the data frame, such change occurs early in the data frame, whereas a change that occurs in the last word of the data frame, occurs late in the data frame. Given this restriction, one aspect of the present invention relates to mapping the particular electrode pair associated with the words of the data frame so that the electrode pair in contact with the basal end of the cochlea, which receives high frequency information and thus has the most information capacity, is mapped to the first word in the data frame. The apex of the cochlea, which receives low frequency information and thus has the least information capacity, is mapped to the last word in the data frame. This mapping scheme, in combination with sending partial frames (as described in the '617 patent) advantageously permits a two-to-three times faster update rate to occur at the base of the cochlea than has heretofore been possible.

It should be noted that the stimulation pattern depicted in FIG. 5 represents a simple (non-complex) stimulation pattern. Simple and easy-to-define stimulation templates (or "pulse templates") are used to permit the SP and ICS to generate much more complex stimulation patterns without having to significantly alter the basic operating programs of the speech processor 16, and without having to alter the circuitry of the ICS 12. In fact, the stimulation templates may advantageously be used with any type of stimulation system that provides an implanted stimulator that follows the commands of an external processor in a master/slave relationship. That is, so long as the individual channels (or specific tissue stimulation locations as defined by a selected electrode pair) of the implanted stimulator can be set to a specific stimulation current value (including a zero value) as controlled by a control processor, and remain at those values until reset by the control processor to a new stimulation current value, then the present invention can advantageously be used by such system.

Figure 6:
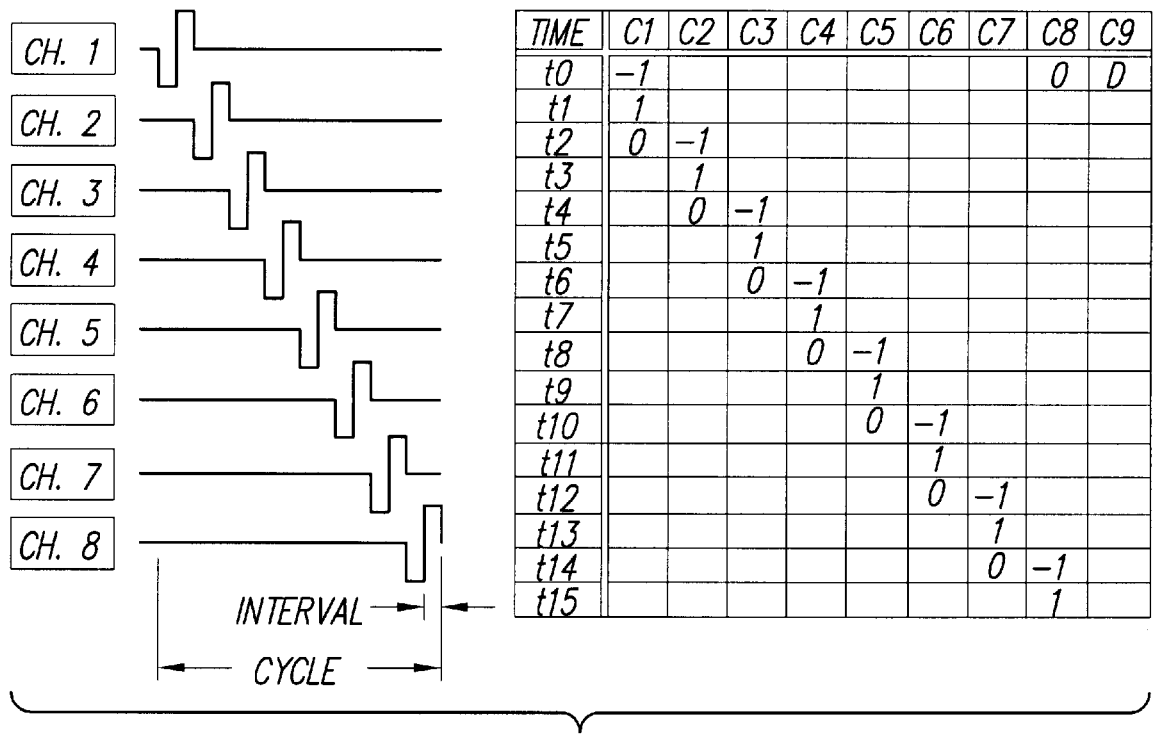
FIG. 6 illustrates a stimulation template that may be used with the invention to produce one form of a continuous interleaved sampler (CIS) speech processing strategy that provides a CIS stimulation pattern for an eight-channel cochlear stimulator.

To illustrate, FIG. 6 shows one representation of a simple biphasic CIS stimulation template for use with the present invention that provides a CIS stimulation pattern for an eight-channel stimulator device. The template is in the form of a stimulation table, shown on the right side of FIG. 6, which table may be stored in the memory 31 of the processor 16 or elsewhere. The biphasic stimulation currents that result from using such template are represented on the left side of FIG. 6. Note that the stimulation table or template comprises rows and columns. Each row represents an increment of time, which increment of time may be set to an appropriate value for the particular application. For the table shown in FIG. 6, it is presumed that all of the increments of time, t0–t15, are equal increments of time. However, as demonstrated by other possible templates shown in the '617 patent, the time increments need not be equal, but can be specified to any appropriate value.

Each column of the template table shown in FIG. 6 represents a channel, or stimulation location, Thus, referring to FIG. 6, it is seen that each cell (i.e., each intersection of a row and column) of the template table defines a particular stimulation current that is to be applied to a specific location (the channel, or column) at a particular time (the specified time, or row). The combination of all the cells of the template table thus defines a particular spatiotemporal stimulation pattern, or a particular cycle of stimulation waveforms, that are to be applied to specific stimulation locations at specific times within the stimulation cycle.

The numerical values inserted into the cells of the template table represent weighting factors which are to be used to modify the amplitude of the processed signals (derived from the incoming acoustical signal). (It should be noted that data values other than numeric values could also be used for this purpose, e.g., a hexadecimal or other alphanumeric value could be inserted into the cells of the template table as a code.) A null value (blank) table cell indicates that a zero stimulus waveform has been in effect and should continue in effect for the channel and time specified by the column/row of the template. Typically, the weighting factor will simply be used as a multiplication factor. Thus, if the template table contains a "+1" in a given cell, then that means the processed signal for that channel is to be multiplied by a "+1", with the product of such multiplication serving to define or specify the amplitude of the desired stimulation current to be applied to the electrode pair of the channel at the indicated time increment. An explicit zero, or "0", denotes the time at which a previously non-zero channel is first set to zero output.

It is to be emphasized that the rows and columns of the template table can be reversed and the template table will still serve its intended function of clearly and easily defining a particular stimulation pattern, even a complex stimulation pattern (as is demonstrated below) for use by an ICS or equivalent stimulator device. That is to say, each column of the table may represent an increment of time, and each row of the table may represent a channel, or stimulation location.

Referring to FIG. 6, it is seen that at time t0, the first channel, C1, has a value "−1" inserted therein. All other cells in the table at time t0 are blank (null values), except for C8 (which has a "0" inserted therein), and C9 (which corresponds to the control column or word and which has a "D" inserted therein). The "−1" in the cell corresponding to channel C1 at time to means that whatever magnitude is present in the channel 1 signal at time t0 will be multiplied by a "−1". The "0" simply means that channel C8 is to be reset back to zero (null) at time to. The "D" in channel C9 (which is the control word channel) means that the 9th word command is to be set to its default value. At time t1, the weighting factor for channel C1 changes to a "+1". At time t2, the weighting factor for channel C1 is set to "0", and the weighting factor for channel C2 is set to "−1". The timing associated with the actual waveforms for the stimulation currents thus take the form as illustrated on the left side of FIG. 6.

Figure 7:
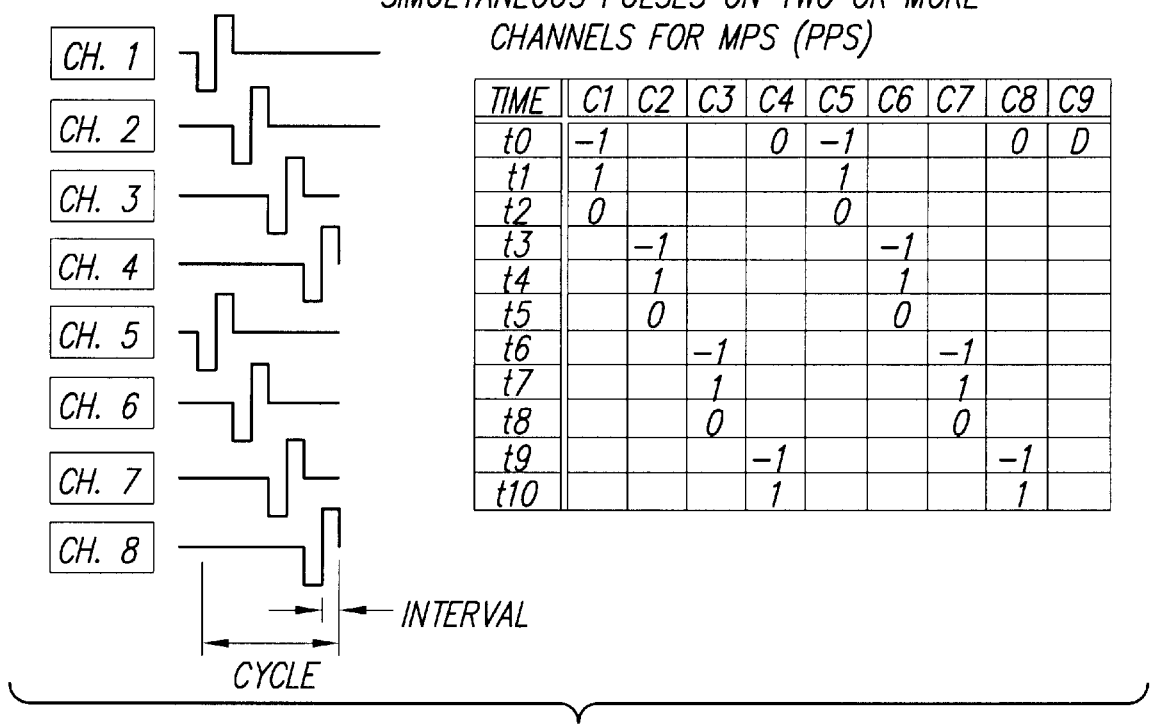
FIG. 7 illustrates a stimulation template that may be used with the invention to produce a paired pulsatile sampler (PPS) speech processing strategy that provides a PPS stimulation pattern for an eight-channel cochlear stimulator.

FIG. 7 depicts a stimulation template for a stimulation pattern that provides simultaneous biphasic pulses on two or more channels, thereby providing one type of multiple pulsatile stimulation (MPS). Such a pattern allows the overall cycle length to be decreased significantly. The stimulation pattern shown in FIG. 7 is of particular interest because of the delivery of pulses more or less simultaneously at two or more different sites. Note that the CIS strategy is designed to minimize electronic interactions between the stimulus currents applied at adjacent sites by delivering brief stimulation pulses in a sequential, interleaved, i.e. non-overlapping manner. It is also desirable, however, to complete the stimulation of all sites in as short a cycle time as possible, permitting the information from the acoustic signal to be sampled and presented at a relatively high rate. In order to sequence through a large number of stimulation sites at a relatively rapid rate, the length oftime available to deliver each individual stimulation pulse must be made very short. The efficacy of a given stimulus pulse in activating neurons depends on the product of the magnitude and duration of the current, i.e. the total charge delivered in each phase of the waveform. In order to activate neurons with a very brief current pulse, the magnitude of the current must be made proportionately higher. Because the electrode contacts and surrounding tissue represent a significant impedance to the flow of electrical current, the applied voltage and dissipated power will also be much higher. The problem is even worse for biphasic stimulus pulses shorter than about 60–80 microseconds because the reverse polarity of the second phase partially cancels the effects of the first phase before the neurons can respond to the first phase.

Advantageously, as shown in FIG. 7, the CIS frame rate for a given number of channels each with a given pulse width can be doubled by stimulating two separate sites at the same time. This two-pulses-at-the-same-time approach (referred to herein as "paired pulsatile sample, or PPS" is best used when the amount of electronic interaction between those sites is minimal. That condition is likely to be met when the simultaneously activated sites are selected to be physically distant from each other and when the intensity of stimulation required to produce a full range of loudness at each site is fairly low. Thus, it is a particular advantage of the invention that the pattern of overlap between pulses at various sites can be readily selected and changed simply by altering the values in the template table rather than reprogramming a new algorithm for each stimulus paradigm or pattern.

Figure 8:
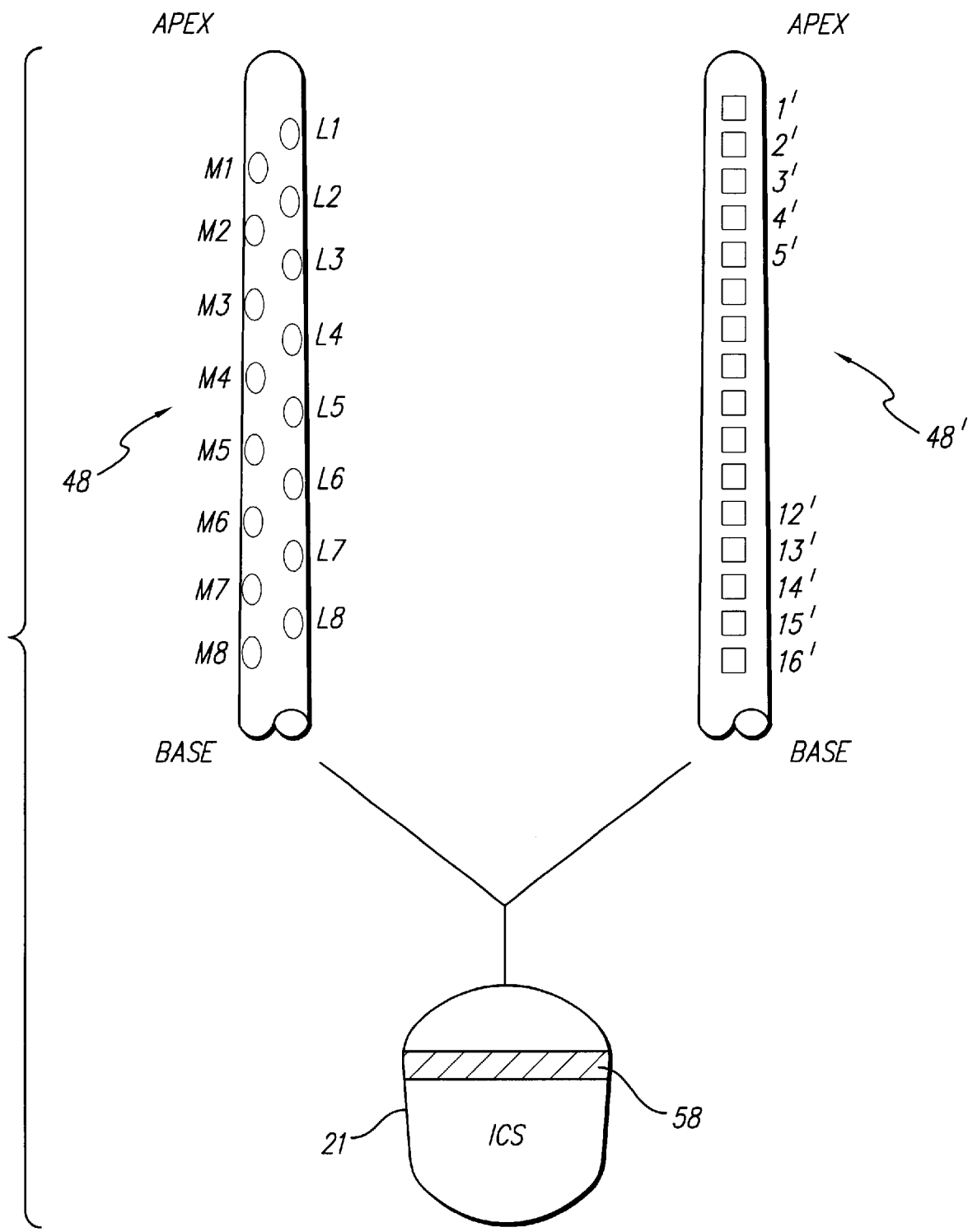
FIG. 8 schematically illustrates two types of electrode arrays that may be used with an ICS, wherein by way of example each electrode array has sixteen individual electrode contacts, and wherein a common or reference electrode contact is provided on the case of the ICS.

It should also be noted that stimulation templates of the type shown in FIGS. 6 and 7 may also be readily used to create multiphasic pulses. An example of a triphasic pulse, for example, is shown in FIG. 8 of U.S. Pat. No 5,601,617, previously incorporated herein by reference. Once one understands the basic premise of how such stimulation templates are used, there is no limit to the type of pulse pattarns that may be created using such templates.

An alternate type of data frame to that shown in FIG. 4 is described in copending patent application Ser. No. 09/322, 721, filed concurrently herewith, and previously incorporated herein by reference. This referenced patent application, which is entitled "Multichannel Cochlear Prosthesis With Flexible Control of Stimulus Waveforms", describes, inter alia, an alternative embodiment for the implantable cochlear stimulator (ICS) portion of a cochlear implant system referred to as the "S2" ICS. Again, it is to be emphasized that the present invention may be used with any type of cochlear implant system, whether such implant system uses an ICS of the type described in U.S. Pat. No 5,603,726, an S2 ICS of the type described in the referenced patent application 09/322/711, a totally implantable system of the type disclosed in U.S. patent application Ser. No. 09/126,615, filed Jul. 31, 1998, also previously incorporated herein by reference, or other types of cochlear prosthesis and systems.

Turning next to FIG. 8, there is shown a schematic representation of two types of electrode arrays 48 and 48' that may be used with a cochlear implant system. Other types of electrode arrays could also be used with a cochlear prosthesis, e.g., of the type shown in U.S. Pat. Nos. 4,819, 647 or 5,000,194. The arrays 48 and 48' of the type shown in FIG. 8, however, represent preferred arrays that may be used. It should be noted that the present invention is not limited to any particular type of electrode array. Rather, as explained below, any type of array that may be represented or depicted in a graphical display that allows the type of electrode coupling that is used to be indicated on the display, e.g., bipolar or monopolar, may be used as part of the invention. In FIG. 8, either type of electrode array 48 or 48' has its proximal end (not shown) connected to an ICS 21. This connection enables the current generators within the ICS for each channel to apply a current stimulus of a desired amplitude, polarity, duration and repetition rate to be applied to the paired electrode contacts for that channel.

In one embodiment, the electrode array 48 includes sixteen electrode contacts, identified in FIG. 8 as M1, L1, M2, L2, M3, L3, . . . M8, L8. As seen in FIG. 8, the electrodes identified as M1, M2, M3 . . . M8 are on the medial side of the electrode; and the electrodes L1, L2, L3, . . . L8 reside on a lateral side of the electrode. The output circuitry within the ICS 21 may be configured so as to connect selected pairs of these electrodes to provide bipolar stimulation. One form of bipolar stimulation, referred to as radial bipolar, pairs electrode contacts L1 with M1, L2 with M2, and so on, through L8 with M8. Another form ofbipolar stimulation, referred to as enhanced bipolar, pairs electrode contacts M1 with L2, M2 with L3, M3 with L4, M4 with L5, M5 with L6, M6 with L7, M7 with L8, and M8 with L1. Using bipolar electrode coupling, i.e., applying the stimulating electrical pulses through paired electrode contacts that are adjacent each other on the electrode array 48, provides a more focused stimulation that is typically used with a simultaneous speech processing strategy, e.g., a simultaneous analog speech processing strategy, such as SAS.

Additionally, a reference or common electrode 58 may comprise an exposed portion of a band on the case of the ICS 21. Through use of such reference electrode 58, it is thus also possible to configure the system for monopolar stimulation. In monopolar stimulation, a first channel may pair electrode contact M1 or L1 with the reference electrode, a second channel may pair electrode M2 or L2 with the reference electrode, and so on, with the eighth channel pairing electrode M8 or L8 with the reference electrode. Using monopolar electrode coupling, i.e., applying the stimulating electrical pulses through paired electrode contacts that include the distant reference electrode, provides a less focused stimulation that is typically used with non-simultaneous speech processing strategies, such as CIS.

Additionally, as described above in connection with FIG. 3E, virtual coupling may also be employed through appropriate mapping of the SP analysis channels with the ICS stimulation channels in order to fine tune the position or location where a stimulus excites neural tissue.

Monopolar, bipolar or virtual coupling may also be used with an electrode array 48', also shown in FIG. 8. The array 48' has all of its electrode contacts, 1', 2', 3', . . . 15', 16', along a medical side of the array. A typical bipolar coupling used with the array 48' pairs electrodes 1' and 2', 3' and 4', 5' and 6', and so on, through 15' and 16'. A typical monopolar coupling for the array 48' will pair electrodes 1', 3', 5', . . . 15' with the reference electrode 58; or electrodes 2', 4', 6', . . . 16' with the reference electrode 58.

At this point in the description of the invention, reference will be made to FIGS. 9–16, where there is shown exemplary selection and/or measurement screens that may be used as part of a fitting session as an aid in selecting one of a plurality of speech processing strategies, or while performing other measurements or settings. It is noted that many different types of fitting systems and/or software-controlled fitting techniques and approaches could be used with a multichannel cochlear implant system during a fitting session. Within the guidelines presented below, the details of the particular fitting system used for this purpose are not deemed important for purposes of the invention. Such details may be, e.g., as described in the previously referenced Device Fitting Manual, provisional patent application (Serial No. 60/087,656), the previously referenced U.S. Pat. No. 5,626,629 , otherwise formulated from the descriptions of FIGS. 9–16, which follow. Hence, FIGS. 9–16 are presented below to depict a preferred type of selection or measurement screen that may be used as part of a fitting session or as an aid or tool in selecting one of a plurality of available speech processing strategies for use by the cochlear stimulation system. The selection screens illustrated in FIGS. 9–16 are thus not meant to be limiting, but are presented solely by way of example. It is submitted that those of skill in the software programming arts could readily fashion many different types of selection and measurement screens that would achieve the same overall objectives as the exemplary screens shown in FIGS. 9–16.

In general, a typical "fitting" session (where the term "fitting" refers to making the appropriate adjustments and settings within the speech processor and/or ICS so that the patient can effectively discern audio signals as sound) in accordance with the present invention involves the steps set forth below. Preliminarily, before carrying out such steps, appropriate patient data will usually be gathered and entered into the computer (e.g., to create a patient "file" that is stored in the fitting computer or processor, and in which file the patient's fitting data may be stored), unless such patient data has already been gathered and entered into the computer, in which case the patient's file is simply 'opened' to begin the fitting session. Once the patient's file has been created or opened, the fitting session or fitting method performs the following steps:

(a) a suitable fitting processor, e.g., a laptop computer, a PalmPilot® hand-held processor, or equivalent, is connected or coupled to a working ICS system, which system includes at least an implantable cochlear stimulator (ICS), an electrode array, and a speech processor (SP), as shown in FIGS. 2A or 2B;

(b) a list of available speech processing strategies is displayed on a display screen of the fitting processor;

(c) from the list of available speech processing strategies, a potential speech processing strategy is selected for use by the ICS;

(d) the spatiotemporal characteristics of the selected potential speech processing strategy are displayed on the display screen, the spatiotemporal characteristics including a representation of the electrode coupling and a representation of the stimulation waveform;

(e) steps (c) and (d) are repeated, as required, to provide information about each potential speech processing strategy;

(f) one of the potential speech processing strategies is then selected as the speech processing strategy of choice to be used by the ICS;

(g) a first set of control signals are generated within the laptop computer or other processor and sent to the speech processor that cause the selected speech processing strategy to be used by the speech processor;

(h) audio signals are applied to the speech processor through the fitting processor and/or the microphone, and second control signals are generated therefrom as a function of the applied audio signals and selected speech processing strategy;

(i) the second control signals are sent to the ICS;

(j) electrical stimuli are applied to the patient through the electrode array as defined by the second control signals to produce the sensation of sound for the patient;

(k) feedback information is received from the ICS and/or the patient that characterizes the patient's response to the electrical stimuli applied in step (j) as sensed by the ICS and/or as sensed by the patient;

(l) the second control signals are adjusted, as required, in response to the feedback information received in step (k) in order to enhance the ability of the patient to sense the audio signals applied in step (h); and (m) steps (h) through (k) are repeated, as required, to improve the patient's ability to sense the audio signals applied in step (h) and correctly perceive these sensed audio signals as sound.

Once the above fitting process has been carried out for one selected speech processing strategy, it may be repeated for other selected speech processing strategies, as required, until the clinician or audiologist, in consultation with the patient, are satisfied that the most effective speech processing strategy has been selected. The speech processing strategy that is most effective will generally be the one that is most comfortable for the patient and which allows the patient to most accurately perceive sounds.

Figure 9:
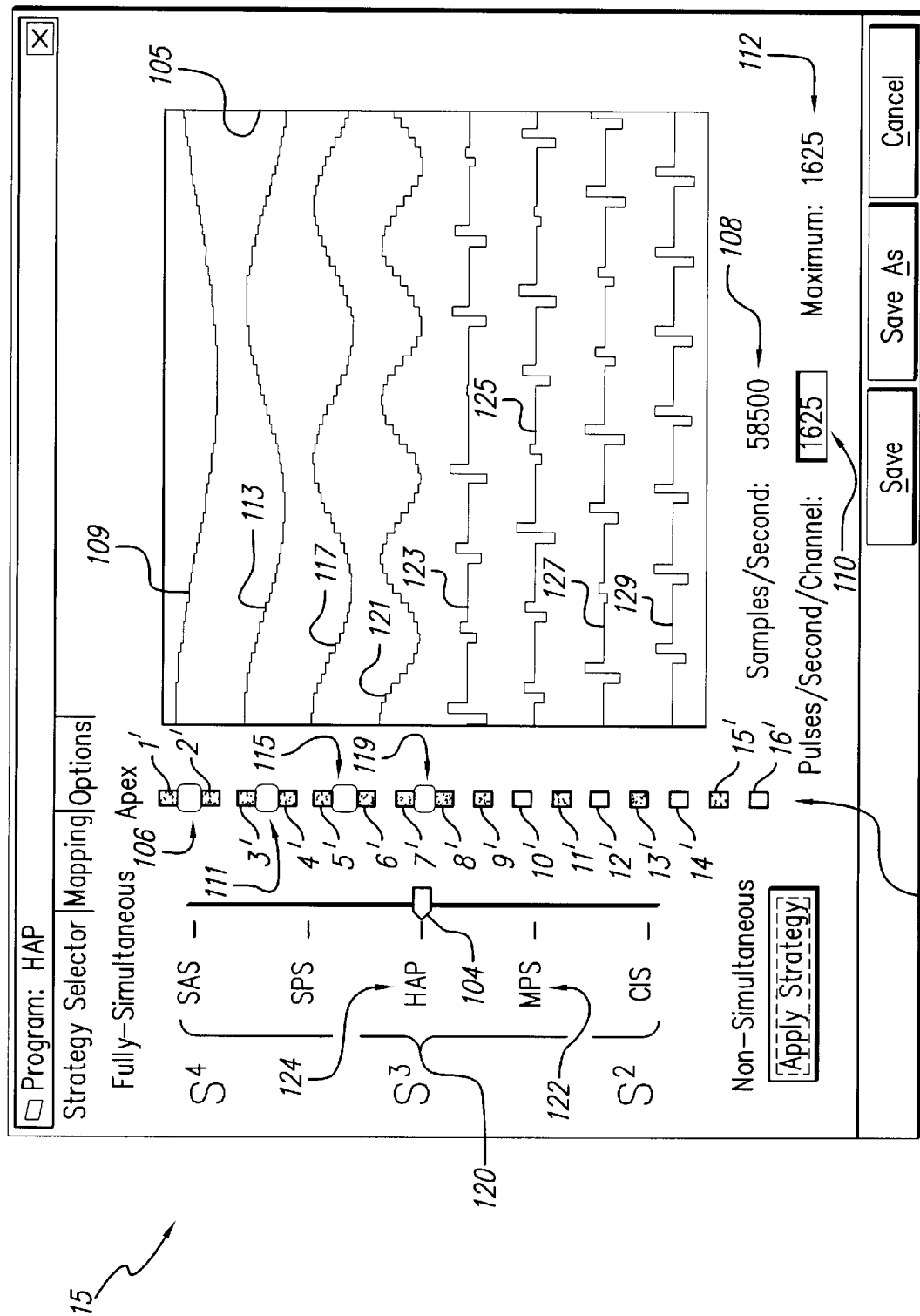
FIG. 9 shows a representative selection screen display provided on a personal computer (PC), or equivalent device, by the invention to facilitate selection of one of a multiplicity of speech selection strategies, ranging from a simultaneous speech processing strategy, e.g., SAS, to a non-simultaneous speech processing strategy, e.g., CIS, and illustrates the various features associated with such selection screen.

With the foregoing as a foundation, the preferred manner in which one of a multiplicity of speech processing strategies is selected as part of an overall fitting session will next be explained in connection with, e.g., the description of FIG. 9. FIG. 9 depicts a universal strategy selector (USS) screen that is displayed on a screen 15 of computer 17 (see FIG. 2) during a typical fitting operation. Advantageously, the selection screen shown in FIG. 9, or equivalents thereof, defines the scope of the speech processing capabilities of the cochlear stimulation system according to the following parameters:

degree of simultaneity number of analog/pulsatile channels pulse pattern number of maxima electrode coupling envelope detection firing order number of channels repetition rate.

The USS screen shown in FIG. 9 may be one of the first screens that appears when one selects to open a "Program" file from a Main fitting session screen. As seen in FIG. 9, a slider 104 on left side of the screen provides manual selection of the speech processing strategies listed along a continuum of simultaneity, from "Fully Simultaneous" at the top to "Non-Simultaneous" at the bottom. For the example shown in FIG. 9, the slider 014 is positioned to select the "HAP" strategy, which is described more fully below. Advantageously, the strategies are also grouped into commonly-identified stimulation categories ($S^4$, $S^3$, $S^2$) that represent fully-, partially-, and non-simultaneous processing. When a color monitor is used, the $S^4$, $S^3$, $S^2$ categories of the different strategies may be color coded as different shades, e.g., different shades of blue.

Also included on the USS screen shown in FIG. 9 is a channel display window 105 wherein the stimulation waveforms are illustrated for each stimulous channel. The stimulous channels, in turn, are defined by a display 107 of an electrode array. The electrode array shown in the representative display of FIG. 9 comprises an electrode array 48' (see FIG. 8), having electrodes 1', 2', 3', . . . 15', 16' located on a medial side, with electrode 1' being located closest to the apex of the electrode. Other displays may include an electrode array 48 (see FIG. 8) having offset electrodes L1, M1, L2, M2, . . . L8, M8. Individual stimulous channels may be turned off/on by clicking on the electrode contacts 1', 2', 3', . . . 15' 16', shown on the electrode display 107, which electrode contacts are shaded to represent the current state of electrode coupling. For example, for the exemplary selection screen shown in FIG. 9, the area between electrode contacts 1' and 2' of the electrode display 107 is brightened, i.e., a bright spot 106 (a bright spot is represented in FIG. 9, as well as other figures, by a square drawn with a light line) appears between the display of electrode contacts 1' and 2'. Such bright spot signifies that electrode 1' is coupled to electrode 2' to provide bipolar coupling for the analog stimulous waveform 109 that is applied to a first stimulous channel, displayed at the top of the channel display window 105. Similarly, a bright spot 111, between the display of electrode contacts 3' and 4', signifies that electrode contacts 3' and 4' are paired together to provide bipolar coupling through which an analog waveform 113 is applied to a second stimulous channel, displayed in the channel display window 105 below the waveform 109. In like manner, bright spot 115 signifies that electrode contacts 5' and 6' are paired bipolarly to produce analog stimulous waveform 117 in a third stimulous channel; and bright spot 119 signifies that electrode contacts 7' and 8' are paired bipolarly to produce analog stimulous waveform 121 in a fourth stimulous channel.

Still with reference to the exemplary selection screen of FIG. 9, it is seen that the display of electrode contact 9' is shaded dark, while the display of electrode contact 10' is shaded lighter. The dark shading of the display of electrode contact 9' signifies that electrode contact 9' is tuned off, while the lighter shading of the display of electrode contact 10' signifies that electrode contact 10' is paired monopolarly with the reference electrode 58 (see FIG. 8). (Note, in a color display, an electrode contact that is off, such as contact 9', may be represented with one color, e.g., grey, while an electrode contact that is on, such as contact 10', may be represented with a contrasting color, e.g., blue.) The monopolar coupling of electrode 10' with the reference electrode 58 is associated with a pulsatile waveform 123 in a fifth stimulous channel displayed in the channel display window 105. Similarly, monopolar coupling of electrode 12' with the reference electrode 58 is associated with a pulsatile waveform 125 in a sixth stimulous channel; monopolar coupling of electrode 14' with the reference electrode 58 is associated with a pulsatile waveform 127 in a seventh stimulous channel; and monopolar coupling of electrode 16' with the reference electrode 58 is associated with a pulsatile waveform 129 in an eighth stimulous channel.

Thus, as seen in FIG. 9, for the particular strategy selected ("HAP"), the top four stimulous channels shown in the channel display window 105 provide simultaneous analog stimulation; while the bottom four stimulous channels provide sequential pulsatile stimulation.

Additionally, as needed, a menu may be made available by right clicking while pointing at the display 107 of the electrode array. Such menu allows any of the following firing orders to be selected: Base to Apex, Apex to Base, Staggered, or Jittered. Only one firing order may be selected at any given time.

When selected by the slider 104, right-clicking on "HAP" (hybrid analog pulsatile") allows the user to specify the number of analog channels to be used with the HAP strategy. Of eight available channels, for example, as few as one, or as many as seven, may be selected as analog channels for a HAP strategy selection. The channels not selected as analog channels, unless disabled, will be pulsatile channels. The pulsatile channels may be specified as having pulse patterns that are non-simultaneous, paired, quadrupled, or fully simultaneous. Thus, it is seen that it is possible to customize the selected strategy to suit the individual needs of the patient.

Thus, as described above, it is seen that a key feature of the invention is that the waveforms for the different channels are displayed concurrent with the selection mechanism, e.g, the slider 104, as a function of the strategy currently selected by the selection mechanism. This allows the person making the selection to visualize the precise type of spatiotemporal stimulation pattern that is being provided over all of the channels. This display of the waveforms is presented in the channel display window 105, as described above, and includes showing a representation (not to scale) of the amplitude and width of the stimuli. Moreover, through the use of the toolbox, the clinician or audiologist may select between full and half-wave rectification. Right clicking on a particular waveform allows the clinician to select between off/on or envelope detection, and also to turn the stimulous channel on or off.

The sampling rate associated with the particular strategy is displayed along the bottom of the display at area 108. The repetition rate per channel ("pulses/second/channel") is also displayed along the bottom of the display at box 110, with the maximum allowable rate stated beside it at area 112. The clinician may select a desired repetition rate by entering it in the box 110 provided the selected value for the repetition rate is not greater than the maximum allowable.

Preferably, the relative pulse widths of the biphasic or multiphasic pulses used in the pulsatile channels are graphically represented on the waveforms included on the right of the window.

The pulse pattern to be used for MPS and HAP strategies is selected by right-clicking on the strategy when selected. For example, MPS or HAP may use paired or quadrupled (quad) pulse patterns. A paired pulse pattern is one wherein two pulses appear simultaneously on two channels (see FIG. 7), and a quad pulse pattern is one wherein four pulses appear simultaneously on four channels.

Thus, with reference to the representative USS screen that appears as shown in FIG. 9, it is seen that the degree of simultaneity is evident from the list 120 of speech processing strategies. Such list orders the available strategies from "fully-simultaneous", at the top of the list, to "non-simultaneous", at the bottom of the list. Any of the listed strategies may be selected through use of the selector, or slider 104, which slider or selector may be moved by clicking and dragging a mouse, or by pressing specified keys on the keyboard of the computer, or equivalent means.

It is further seen from the USS screen shown in FIG. 9 that the pulse pattern may be selected, e.g., through the selection of a particular pulsatile stimulation pattern, such as an MPS selection (indicated by the arrow 122). Moreover, the pulse pattern and number of analog/pulsatile channels may be specified, e.g., as indicated by the arrow 124, as explained above, for certain of the possible strategies, such as HAP.

Electrode coupling, e.g., bipolar, monopolar odd, or monopolar even for an electrode array 48' (see FIG. 8), or monopolar medial, monopolar lateral, or bipolar for the electrode array 48 (see FIG. 8) may be globally applied from the toolbox or individually selected by right clicking on the individual electrode(s) displayed on the graphical representation 107 of the electrode array. The electrode pairing resulting from a selected or default electrode coupling is illustrated by the coloring or shading of the individual electrode contacts 1', 2', 3', . . . 16', shown on the display. An activated electrode contact 10', for example, may appear highlighted, brighter or a different color than a non-activated electrode contact 9'.

Right clicking on individual electrode contacts 1', 2', 3', . . . 15', 16', causes such contacts to be individually activated or non-activated. Individual channels may be deselected by right-clicking on the appropriate electrode contact (s) for the desired channel so the electrode pair for that channel is non-activated. When a given channel is deselected, the waveform for that channel appears as a straight line in the channel display window 105. Hence, the number of channels to be used at any given time is readily selectable by deselecting unwanted channels.

Figure 10:
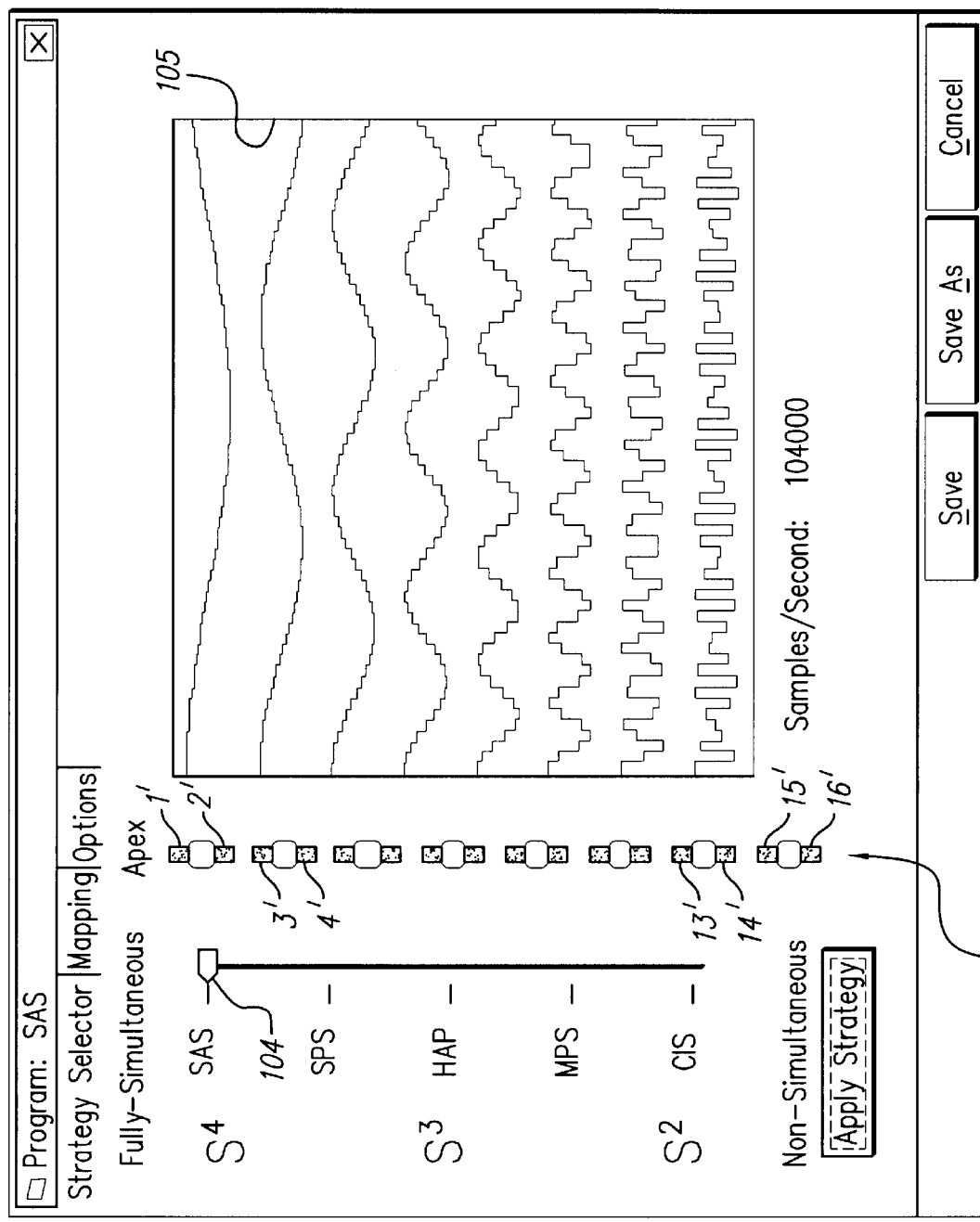
FIG. 10 shows a representative screen display provided by the invention when an SAS strategy is selected, wherein analog stimulation waveforms are applied to all channels simultaneously.

Turning next to FIG. 10, there is shown a representative USS screen display provided by the invention when an SAS strategy is selected by the selector 104. As seen in the channel display window 105, when SAS is the selected strategy, reconstructed analog stimulation waveforms are applied to all channels simultaneously. Note that bright or highlighted spots (represented in FIG. 10 by a square) between electrode contacts 1' and 2', 3' and 4', 5' and 6', 7' and 8', 9' and 10', 11' and 12', 13' and 14', and 15' and 16', show that bipolar electrode coupling is used.

Figure 11:
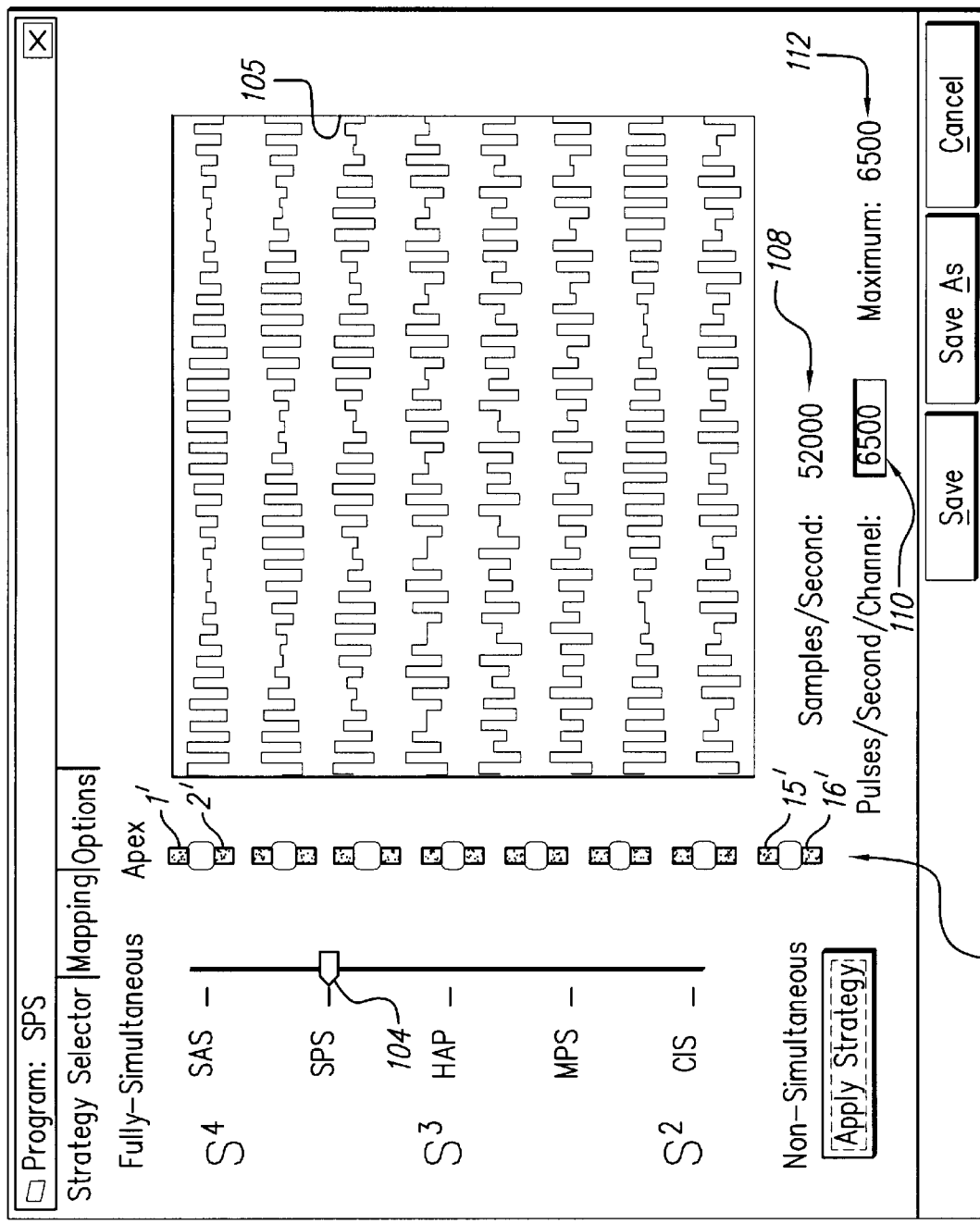
FIG. 11 illustrates the representative screen display provided by the invention when a simultaneous pulsatile sampler (SPS) strategy is selected, wherein biphasic pulses are applied to all channels simultaneously.

FIG. 11 illustrates a representative screen display provided by the invention when a simultaneous pulsatile sampler (SPS) strategy is selected by the selector 104. As seen in the channel display window 105, such SPS selection applies biphasic pulses to all channels simultaneously. The pulses/second/channel may be specified at selection box 110. The sampling rate and maximum pulses/second/channel are then displayed at areas 108 and 112. Of course, as with all the available selections, individual channels may be disabled, so that any of one to eight channels may be stimulated with the SPS speech processing strategy.

Figure 12:
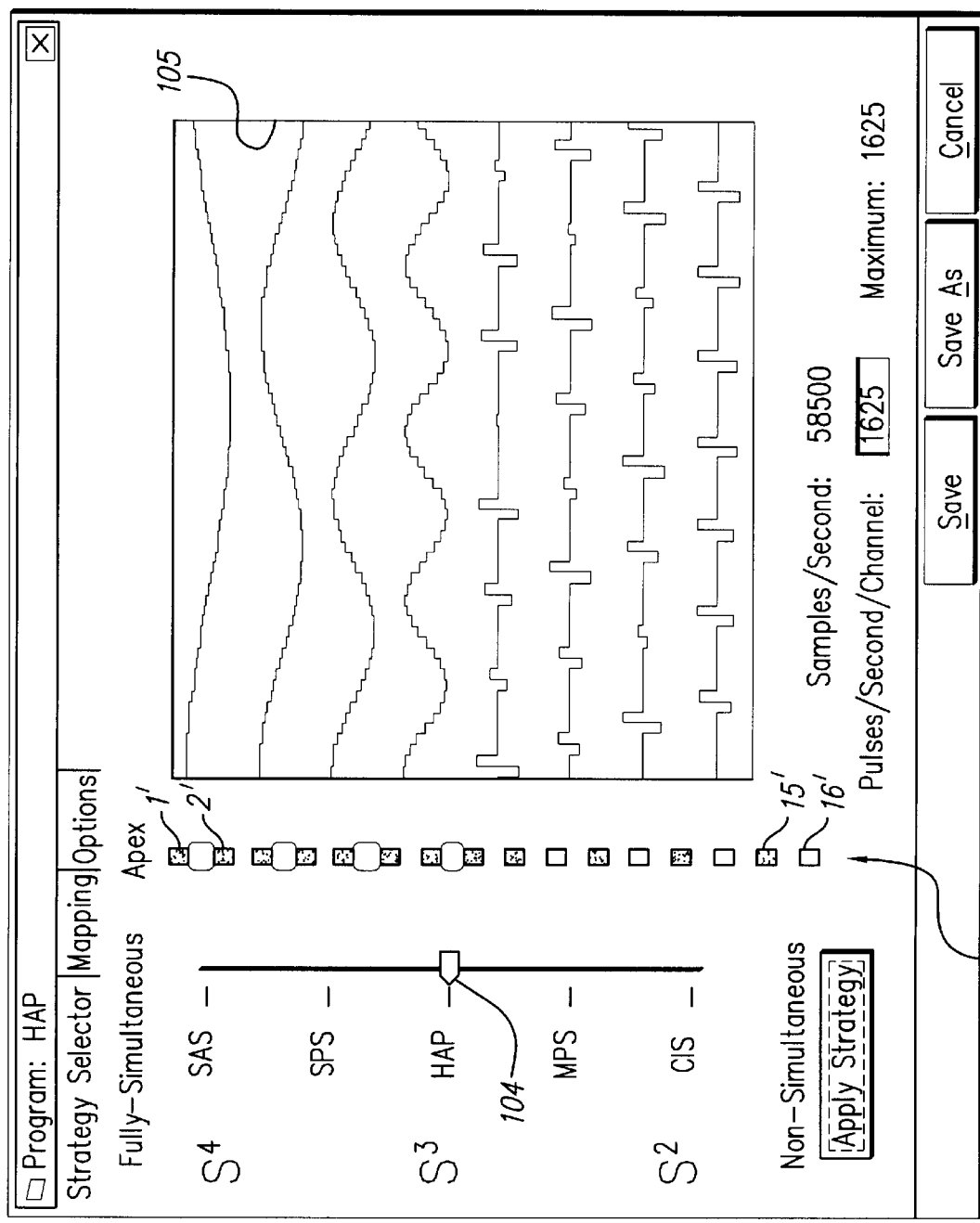
FIG. 12 similarly depicts the representative screen display provided by the invention when a hybrid analog pulsatile (HAP-4) strategy is selected that provides a simultaneous analog strategy on four channels and a sequential CIS-type pulsatile strategy on four channels, of an eight channel cochlear stimulation system.

FIG. 12 similarly depicts the representative screen display provided by the invention when a hybrid analog pulsatile (HAP) strategy is selected. As described above in connection with FIG. 9, a HAP selected strategy provides a simultaneous analog strategy on a selected number of channels, e.g., the four channels closest to the apex of the array, and a sequential CIS-type pulsatile strategy on the remaining channels, e.g., the four channels closest to the base of the array. That which is illustrated in FIG. 12 comprises a HAP-4 strategy, because there are four channels that provide SAS and four channels that provide CIS. As explained previously, other variations of HAP may also be defined, e.g., HAP-1 through HAP-7, wherein from one to seven channels are stimulated with an SAS strategy. Further, as also explained previously, the pulsatile channels may be selected to provide multiple pulsatile stimulation (MPS) strategies other than CIS, e.g., QPS (quad pulsatile sampler) or PPS (paired pulsatile sampler).

Figure 13:
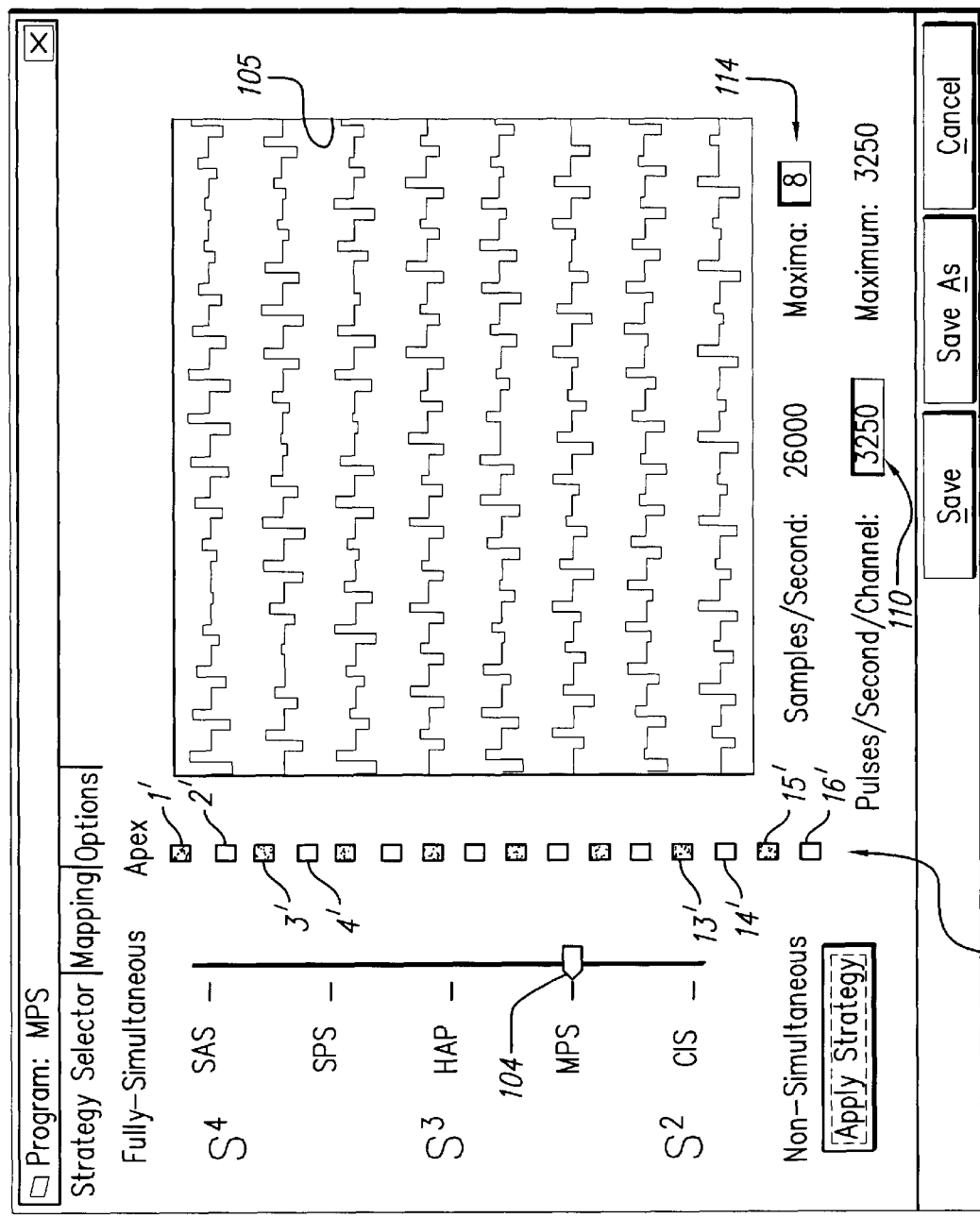
FIG. 13 likewise shows the representative screen display provided by the invention when one type of a multiple pulsatile sample (MPS) strategy is selected, the selected strategy shown comprising a quad pulsatile sampler (QPS) strategy wherein biphasic pulses are alternately applied to four channels simultaneously.

FIG. 13 likewise shows a representative USS screen display when one type of a multiple pulsatile sampler, or MPS, strategy is selected. The particular strategy shown in FIG. 13 comprises a quad pulsatile sampler (QPS) strategy wherein biphasic pulses are alternately applied to four channels simultaneously. That is, as seen in FIG. 13, starting from the top of the channel display window 105, the first, third, fifth and seventh channels have biphasic pulses applied to them at a time period when the second, fourth, sixth and eighth channels do not have biphasic pulses applied to them. Similarly, when the first, third, fifth and seventh channels do not have biphasic pulses applied to them, the second, fourth, sixth and eighth channels 2, 4, 6, and 8 do have biphasic pulses applied to them.

An NofM parameter, which refers to the Number of Maxima that are stimulated per frame, may also be selected for pulsatile strategies through selection box 114. Here, N is the number of maxima to be used out of a possible M channels. The NofM parameter specifies an integer number (N) of maxima to be used out of a possible number (M) of pulsatile channels, wherein the number N defines the number of channels out of the total possible M channels that are stimulated with biphasic pulses during a prescribed time period, e.g., during each frame. While the number of maxima may be selected, an algorithm is typically used to determine which ones of the possible channels are stimulated per frame. A common algorithm selects the N channels with the greatest input levels. Thus, for example, if there are eight channels (M=8) and the maxima is set to six (N=6), then only six channels will be selected for stimulation per frame. However, these six channels may differ from frame to frame, with the six channels with the greatest input levels being usually selected during a given frame. The number of maxima equals the number of channels by default. This NofM parameter is only modifiable with pulsatile strategies such as SPS, MPS and CIS, or (for some embodiments) the pulsatile channels of a HAP selection. The number of maxima can never exceed the number of pulsatile channels. The use of an NofM parameter in this manner for multiple simultaneous pulsatile strategies has never been done before, to applicants' knowledge.

By way of example, in FIG. 13, the number of maxima is set at box 114 to eight, which is the default value. Thus, all eight of the channels shown in the channel display window 105 are selected for stimulation during each frame, which means NofM is really not functioning, i.e., the normal all-channel stimulation is occurring. However, if the number of maxima were set at box 114 to six, then only six of the eight channels shown in the channel display window 105 would be selected for stimulation during a given frame. However, the six channels selected would vary from frame to frame as a function of the controlling algorithm. If the number of maxima were set at box 114 to four, then only four of the eight channels shown in the channel display window 105 would be selected for stimulation during a given frame, with the four channels selected varying from frame to frame as a function of the controlling algorithm.

At this point, it will be helpful to briefly describe one manner in which the NofM feature is implemented in accordance with applicants' preferred embodiment. As explained previously, see, e.g, FIG. 3E, there are analysis channels followed by a selected mapping to stimulous channels. In the analysis channel, the incoming signal is analyzed or otherwise processed in a series of stages. In a first stage, the signal is either analyzed, e.g., the energy content of the signal present in the analysis channel is determined in some fashion, e.g., through the use of an envelope detector; or the signal is simply passed through to the next stage.

Where pulsatile strategies are employed, the preferred implementation of NofM determines the energy content of the incoming signal in a first stage of the analysis channel and then passes the signal to a second stage, comprising essentially a switch, which either allows the signal to continue on or not depending upon the energy detected in the first stage. For pulsatile strategies, a pulse generator generates a train of pulses, e.g., using pulse (or stimulation) template as described previously, in accordance with the selected strategy, which pulses may then be modulated with the detected energy.

In contrast, where analog strategies are employed, the first stage of the analysis channel simply passes the incoming analog signal through to the switch stage, i.e., the envelope detector is disabled, and the switch is enabled to pass the analog signal on to the next stage. Note, that at an appropriate stage in the processing of the analog signal, the analog signal is sampled at an appropriate rate and converted to a digital signal. The digital signal is then mapped to the appropriate output stage(s) of the implanted stimulator, thereby controlling the output stage(s) so that a series of current levels, or stair-step levels, changed or updated at the sampling rate, are applied through the electrodes so as to effectively recreate the analog signal at the stimulous site(s).

The presence of the switch stage within the analysis channels to either enable or disable passage of a signal through to a next stage creates the possibility and capability of using an NofM-type of modulation with analog stimulation strategies. Such analog stimulation strategies may comprise part of what would otherwise be viewed as a fully simultaneous strategy, e.g., SAS, or may comprise part of a hybrid strategy, e.g., an HAP-n strategy. In accordance with such NofM-type modulation, the analog signals, rather than merely being passed through the switch stage, may also be switched on or off as controlled by a specified modulation pattern. Thus, for example, if there are M' analog channels in the selected strategy, any number N' of these M' analog channels could be selected for applying the analog signal through the paired electrodes associated with the stimulous channel during a given time period. The remaining analog channels would be switched off during this time period. The particular N' channels that are switched on during the given time period could be determined by an appropriate algorithm, e.g., a predetermined group of N' channels may be turned on for a first time period T1, and a second predetermined group of N' channels may be turned on for a second time period T2, in a stimulation cycle of T1+T2 seconds. (The stimulation cycle could, of course, also be divided into any number of time periods, e.g., time periods of T1, T2, T3 and T4 seconds, with different groups of channels being on during each time period.) In this way, only N' of the M' analog channels are switched on at any given time, and the N' stimulous channels that are switched on are determined by some controlling algorithm or modulation scheme. Of course, when NofM is applied to analog signals in this fashion, the resulting stimulous signals are no longer true analog signals, but are rather switched analog signals that are present for a specified period of time or are not present as a function of the switching algorithm.

By way of example, switched analog channel stimulation may prove effective relative to improving the comfort level experienced by some patients. That is, some patients may find it helpful (i.e., more comfortable) to have a first group of N' channels providing analog stimulation for a relatively long period of time, e.g., several seconds, and then have a second group of N' channels provide analog stimulation for a relatively shorter period of time, e.g., a fraction of a second. Other patients may simply find it useful, e.g., as part of the fitting process for choosing an appropriate stimulation strategy, including which channels should be active and which channels, if any, should not be active, to have a relatively long testing period (e.g., several minutes) wherein a first group of N' channels provide analog or pulsatile stimulation for a first relatively long period of time, e.g., 20–30 seconds, and a second group of N' channels provide analog or pulsatile stimulation for a second relatively long period to time, e.g., 10–30 seconds, with the ICS automatically toggling between the two groups of channels at a selected rate.

Figure 14:
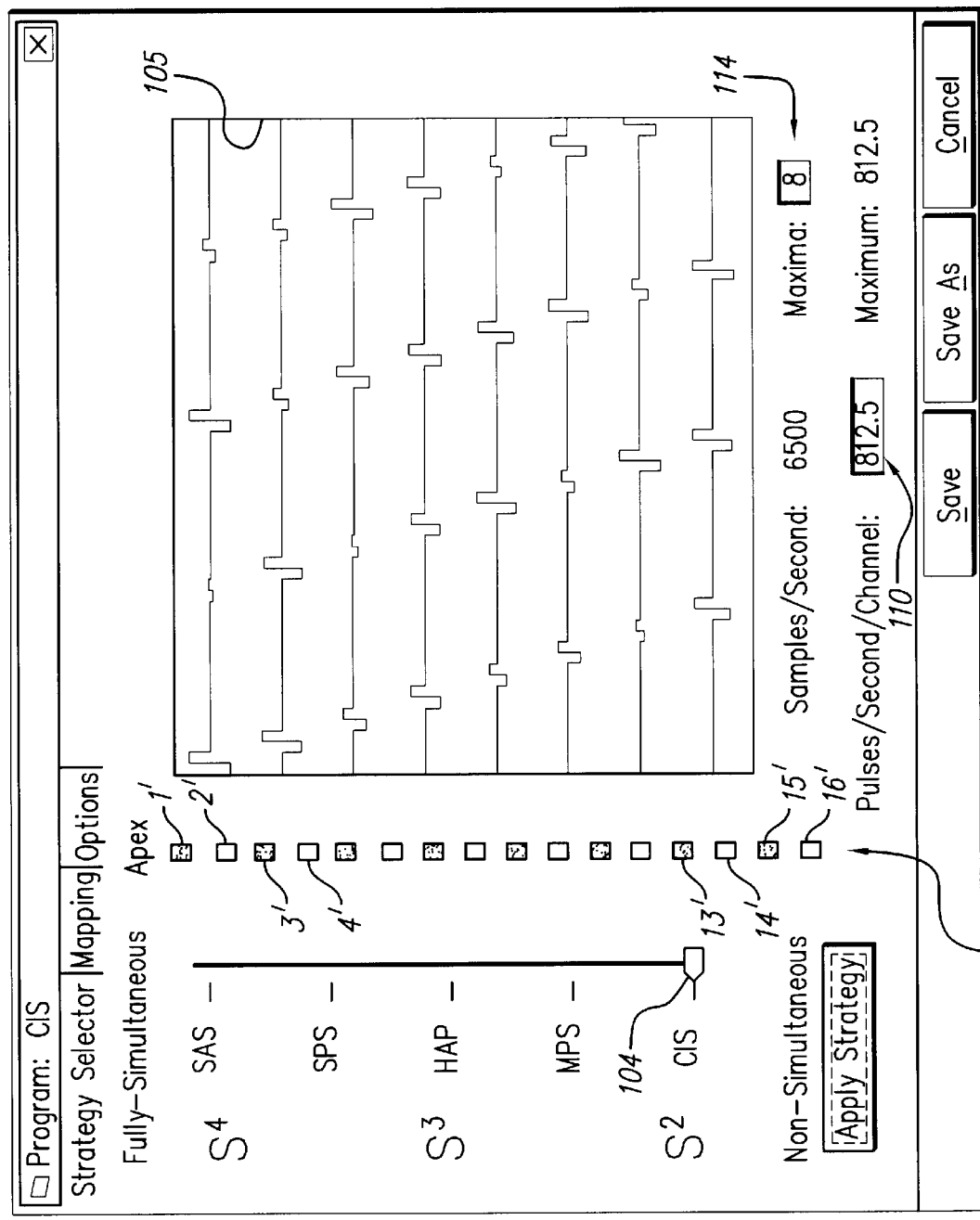
FIG. 14 depicts the screen display provided by the invention when a continuous interleaved sampler (CIS) strategy is applied wherein biphasic pulses are applied in sequence to eight channels, without time overlap, thereby providing a fully non-simultaneous, or sequential, strategy.

Turning next to FIG. 14, there is depicted the screen display provided by the invention when a continuous interleaved sampler (CIS) strategy is applied by the selector 104. This strategy represents the end of the continuum of strategies by degree of simultaneity, with the CIS strategy having no simultaneity. As seen, in a CIS strategy, biphasic or multiphasic pulses (biphasic pulses are shown) are applied in sequence to all eight channels, without time overlap. That is, CIS represents a fully non-simultaneous, or sequential, strategy. As with the other selection options, individual channels within the CIS sequence may be turned off, or disabled, so that the CIS sequence may be selected to cycle through from 1 to M channels, where M is the maximum number of stimulation channels.

For a cochlear stimulation system that does not provide a continuum of strategies from fully simultaneous to sequential, other types of alternative selection screens may be fashioned that order the available stimulation strategies in an appropriate manner. The same salient features of the selection screens described in connection with FIGS. 9–14 above, however, may be implemented on such other screens. For example, a representative display of the stimulation waveform on each channel may be presented, thereby allowing the person making the selection to visualize the precise type of spatiotemporal stimulation pattern being provided over all of the channels. Individual channels may be turned on and off, sampling rates may be set, an NofM parameter may be specified, and relative pulse widths may be defined, all of which are examples of other characteristics of a pulsatile stimulation strategy that may be used in conjunction with the selection screen.

Figure 15:
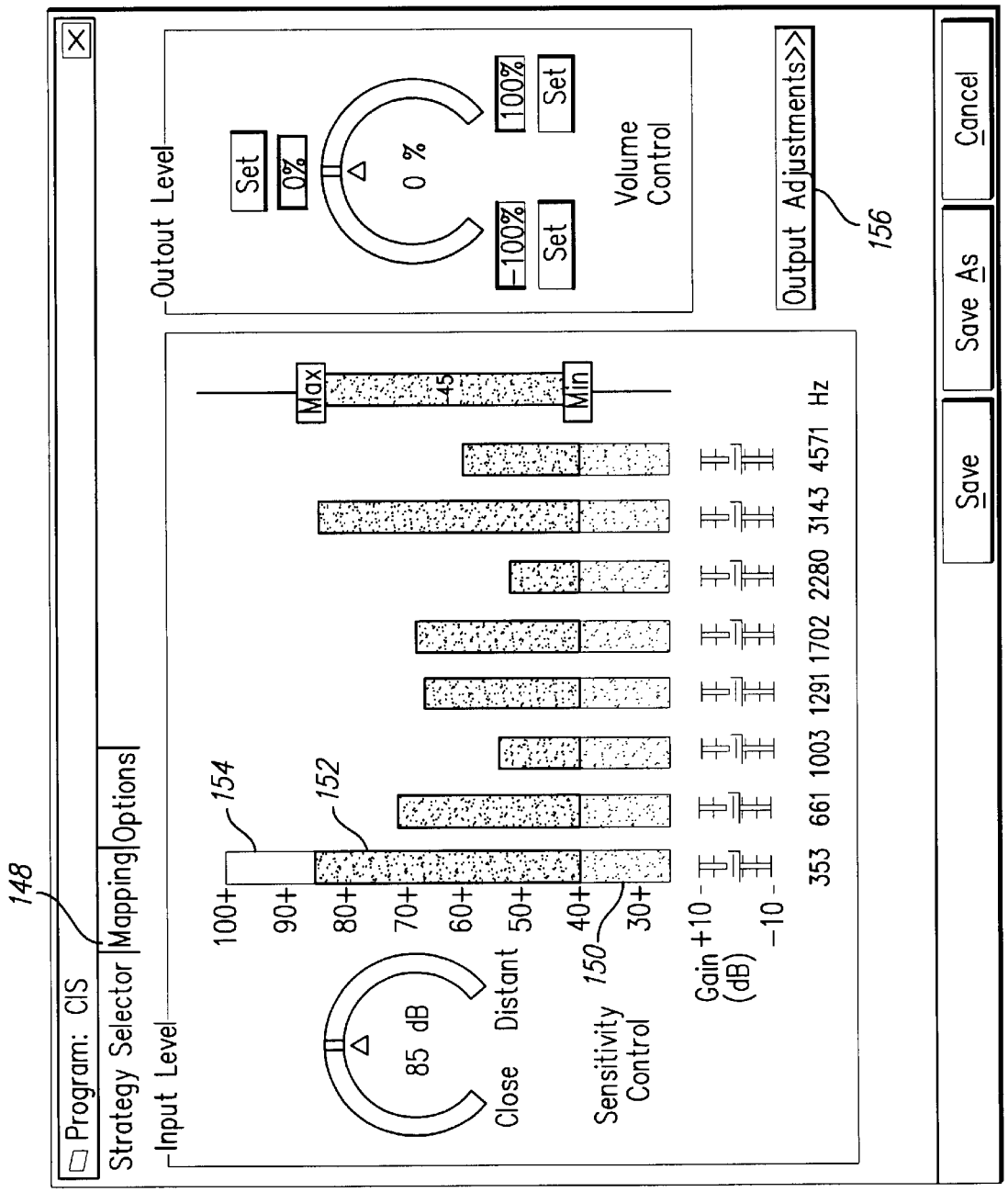
FIG. 15 shows a representative window mapping screen display that may be selected and used by the audiologist or other personnel during a fitting session.

Turning next to FIG. 15, there is shown a representative acoustic mapping screen that may be displayed when selected by the audiologist or other personnel during a fitting session. Such selection is typically made by clicking on the "Mapping" tab 148 located near the top of the display. Although not directly related to the universal strategy selector described above in connection with FIGS. 9–14, the acoustic mapping screen does form a key tool used during a typical fitting session because it allows the audiologist to set the thresholds and other parameters associated with how effectively the patient is able to perceive sound from the simulations that are presented. Thus, in combination with the universal strategy selector described above, the clinician or audiologist is able to use the mapping window to complete a fitting session with a given patient in a relatively short period of time, while still being able to test numerous different types of speech processing strategies in order to find the strategy that is most effective.

The following points represent features or characteristics that are typically made available through use of a preferred mapping screen shown in FIG. 15.

1. Order: The Mapping Window is the typically the next screen accessed by the clinician after selecting a speech processing strategy, as described above.
2. Vu Meter: A VU meter is displayed that represents the acoustic input levels processed by the system
3. Input Levels: The acoustic input levels range from 25 dB to 105 dB.
4. Min & Max Input Levels: The actual range (input dynamic range) that is used by the program is specified by the Min and Max levels. These are the minimum and maximum acoustic input levels that are mapped to the minimum and maximum electrical output levels (T and M levels by default).
5. Vu Meter: A gray area (or medium shaded area) 150 delineates acoustic input levels mapped below the minimum electrical output level (below T).
6. Vu Meter: A green area (or heavy shaded area) 152 delineates the acoustic input levels mapped within the electrical dynamic range.
7. Vu Meter: A yellow area (or light shaded area) 154 delineates the louder acoustic levels that exceed the specified electrical dynamic range (above M).
8. Min Input Level: The clinician can manipulate the minimum acoustic input level, thereby increasing or decreasing the acoustic input range.
9. Sensitivity Dial: When the patient adjusts the sensitivity dial on their speech processor, the entire input range is raised or lowered, reflecting the point at which compression kicks in (kneepoint).
10. Sensitivity Dial: When the sensitivity dial is turned clockwise to hear distant sounds, the range is lowered and the compression kneepoint approaches 75 dB.
11. Sensitivity Dial: When the sensitivity dial is turned counterclockwise to hear only the closer and louder sounds, the range is raised and the compression kneepoint approaches 95 dB.
12. Equalization: The clinician will have access to equalizer tools on the toolbox to globally change the channel input gains.
13. Equalization: Individual channel gain adjustments can also be made by selecting the channel of interest and increasing or decreasing the gain by using the Adjuster tool on the toolbox or the up and down arrow keys.
14. Filters: The center frequencies are listed along the bottom of the screen.
15. Filters: The clinician may change the filter tables on a program by program basis.
16. Firing Order: Firing order options are available from the toolbox for this window.
17. Global Adjustments: The clinician is able to globally adjust the M levels by a percent (%) of the electrical dynamic range both by manually adjusting the speech processor's volume dial or entering a value which represents the adjustment (%) above or below the original M levels.
18. Volume Dial: The upper and lower volume range is be set by turning the volume dial and clicking on Set or manually entering a % value.
19. Volume Dial: By right-clicking on the volume dial picture, the clinician has the option of setting the volume range to default narrow or wide range settings or disabling the dial.
20. Output Adjustments: The original psychophysical T and M levels are never changed. The upper and lower levels of stimulation are modified (adjusted T and M levels).
21. Output Adjustments: By clicking on the Output Adjustments button 156, a screen (see FIG. 16) opens up which displays the original T and M values and the modifications to the levels on each channel.

Figure 16:
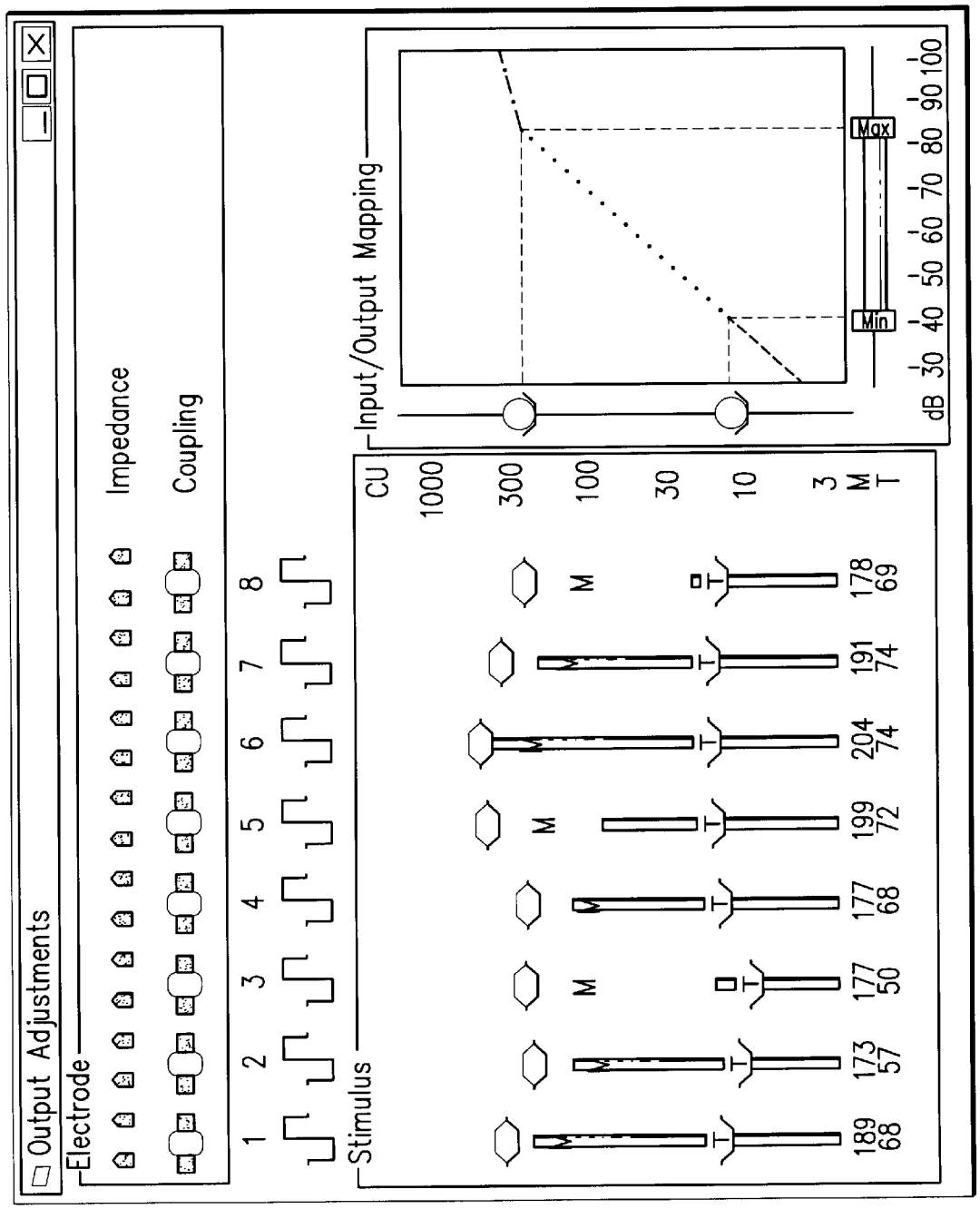
FIG. 16 similarly shows a representative output adjustment screen display that may be selected and used by the audiologist or other personnel during a fitting session.

Turning next to FIG. 16, there is shown a representative output adjustment screen display that is selectively available to the clinician or audiologist as he or she carries out a fitting session. The following points may be made concerning the output adjustment screen:

1. Purpose: The output measurement screen reflects the output levels and allows the clinician or audiologist to tweak output mapping.
2. Global Adjustments: When global adjustments are made to the M levels in the acoustic mapping window, they are reflected in the output adjustment screen.
3. Channel Adjustments: Individual channel adjustments to the stimulus output are made by highlighting the appropriate icons and using the up and down arrows on the keyboard or adjuster buttons on the toolbox.
4. Global Adjustments: The clinician may also choose to globally adjust the levels by selecting the globe icons to the right of the screen.
5. Compliance Voltage: When levels reach compliance voltage, an indicator may be provided that turns yellow (or other suitable color) to warn the clinician.
6. Impedances: Impedances can be remeasured from the output adjustment screen.
7. Coupling: The coupling mode can be changed in this screen by clicking on the coupling button or by right-clicking along the electrode array.
8. Right-clicking: Right-clicking on the channel of interest can also be used to enable/disable clipping and change pulse width.
9. T & M: Since adjustments to the output levels on this screen only affect program parameters and not the original T and M levels, the clinician may be prompted to remeasure T's and M's in the Measurements Screen every three or six months to maintain an accurate record of T's and M's.
10. Graph: A Stimulus/Acoustic Mapping Function is dynamically illustrated on the right side of the screen. This graph effectively shows how the acoustic input is mapped to output levels.
11. Graph: The Min and Max acoustic input levels along the horizontal axis correspond to the Min and Max levels along the vertical axis in the previous screen.
12. View: If the clinician or audiologist desires, the acoustic input and electrical output screens may be viewed side by side.
13. Graph: Gray, green and yellow sections (represented in FIG. 16 by dashed, dotted, and dashdotted lines, respectively) of the output slope correspond to those same areas in the acoustic input VU meter.

It is submitted that those of skill in the art can readily formulate the code needed to implement the present invention, given the descriptions thereof presented herein. The details of the code are not important, as there are numerous coding techniques and coding languages that may be used by those of skill in the art to implement the strategy selection process presented herein.

As described herein, it is thus seen that the invention provides a system whereby a patient, audiologist, clinician or other medical personnel can readily select and test an appropriate speech processing strategy for effective use within a patient's multichannel cochlear prosthesis.

It is a further seen that the invention provides a fitting method or process whereby an audiologist or clinician may select and test multiple speech processing strategies—ranging from simultaneous analog strategies to non-simultaneous pulsatile strategies—within an implanted multichannel cochlear prosthesis over the course of a relatively short fitting session.

It is also seen that the invention provides an easy-to-use speech processing strategy selection process for use with a multichannel implantable cochlear stimulator that unequivocally and understandably coneys to the individual performing the selection exactly what type of speech processing strategy, including, e.g., its degree of simultaneity, number of analog/pulsatile channels, pulse pattern, number of maxima, electrode coupling, firing order, number of channels and repetition rate, is associated with each possible strategy selection.

While the invention herein disclosed has been described by means of specific embodiments and applications thereof, numerous modifications and variations could be made thereto by those skilled in the art without departing from the scope of the invention set forth in the claims.

What is claimed is:

1. A multichannel cochlear prosthesis comprising;
   an electrode array insertable into the cochlea, the electrode array comprising a flexible carrier on which a multiplicity of spaced-apart electrode contacts are positioned, wherein each electrode contact is connected to a respective wire that passes through the carrier to a proximal end of the carrier;
   a multichannel implantable cochlear stimulator (ICS), the ICS comprising a multiplicity of current generators, wherein each current generator is connected to a respective electrode contact of the electrode array through the respective wire of the electrode contact, and wherein each current generator includes circuitry responsive to control signals for applying a current pulse of a specified amplitude, polarity and duration to its respective electrode contact;
   a speech processor (SP) electronically coupled to the ICS, the SP including electronic circuitry that generates and sends the control signals to the ICS as a function of a selected speech processing strategy and received audio signals;
   microphone means for generating the audio signals received by the SP;
   wherein the control signals generated by the SP produce a pattern of electrical stimulation at the electrode contacts that yields speech intelligibility; and
   selection means for selecting one of a multiplicity of speech processing strategies for use within the SP, wherein the multiplicity of speech processing strategies includes a simultaneous analog stimulation (SAS) strategy, a continuous interleaved sampler (CIS) strategy, and at least one strategy whose temporal characteristics lie somewhere in between fully simultaneous or non-simultaneous, and whose stimulating waveform(s) thus comprise(s) a hybrid combination of analog or pulsatile waveforms.

2. The multichannel cochlear prosthesis of claim 1 wherein the multiplicity of speech processing strategies comprises a multiplicity of pulsatile stimulation strategies, including at least one continuous interleaved sampler (CIS) strategy.

3. The multichannel cochlear prosthesis of claim 1 wherein the multiplicity of speech processing strategies comprises a multiplicity of simultaneous speech processing strategies, including at least one simultaneous analog stimulation (SAS) strategy.

4. The multichannel cochlear prosthesis of claim 1 wherein the multiplicity of speech processing strategies includes a hybrid analog pulsatile (HAP) strategy that stimulates a selected number of channels with an SAS strategy, and other channels with a pulsatile strategy.

5. The multichannel cochlear prosthesis of claim 4 wherein the number of channels stimulated with the SAS strategy and the number of channels stimulated with the pulsatile strategy are selectable.

6. The multichannel cochlear prosthesis of claim 5 wherein the total number of channels is eight, and wherein at least four of the eight channels are stimulated with the SAS strategy and the remaining channels are stimulated with a CIS pulsatile strategy.

7. The multichannel cochlear prosthesis of claim 1 wherein the multiplicity of speech processing strategies includes a simultaneous pulsatile strategy (SPS) wherein each channel is stimulated simultaneously with multiphasic pulses.

8. The multichannel cochlear prosthesis of claim 1 wherein the multiplicity of speech processing strategies includes a multiple pulsatile strategy (MPS) wherein a specified number of channels are stimulated simultaneously with multiphasic pulses.

9. The multichannel cochlear prosthesis of claim 8 wherein the specified number of channels that are stimulated simultaneously with multiphasic pulses is two, providing a paired pulsatile strategy (PPS) that is a subset of the selected MPS.

10. The multichannel cochlear prosthesis of claim 8 wherein the specified number of channels that are stimulated simultaneously with multiphasic pulses is four, providing a quad pulsatile strategy (QPS) that is a subset of the selected MPS.

11. The multichannel cochlear prosthesis of claim 1 wherein at least two simultaneous pulsatile strategies are included within the selected strategies that use multiphasic pulses as part of their stimulation waveforms, and wherein a number of maxima (NofM) parameter is associated therewith, the NofM parameter specifying an integer number (N) of maxima to be used out of a possible number (M) of pulsatile channels, wherein the number N defines the number of channels out of the total possible M channels that are stimulated with multiphasic pulses during a prescribed time period.

12. The multichannel cochlear prosthesis of claim 11 wherein each control signal generated by the SP defines the status of each current generator within the ICS for a data frame time period, and wherein the prescribed time period during which N channels out of M possible channels are stimulated comprises the data frame time period.

13. A universal strategy selector (USS) for use with a multichannel cochlear prosthesis, the multichannel cochlear prosthesis including multiple stimulation channels through which a specific pattern of electrical stimulation, modulated by acoustic signals, and in accordance with a selected speech processing strategy, may be spatiotemporally applied to various locations within a cochlea in order to yield speech intelligibility, the universal strategy selector comprising:
   processing means coupled to the multichannel cochlear prosthesis for defining one of a multiplicity of speech processing strategies for use by the multichannel cochlear prosthesis, wherein the multiplicity of speech processing strategies comprises at least five speech processing strategies;

a selector associated with the processing means for identifying a selected one of the multiplicity of speech processing strategies as the selected speech processing strategy; and a visual display coupled to the processing means;

wherein the processing means further includes means for controlling the visual display so that a graphical representation appears thereon that characterizes the selected speech processing strategy in terms of representative stimulation waveforms and electrode pairing for each channel.

14. The USS of claim 13 wherein the visual display shows a graphical representation of an electrode array, including electrode contacts on the electrode array, and depicts electrode pairing by appropriate shading or coloring of the electrode contacts.

15. The USS of claim 13 wherein the visual display shows the spatiotemporal relationship of the stimulation waveforms applied to each channel by displaying timing-waveform diagrams of stimulation currents applied to each channel, the timing-waveform diagrams depicting a representation of the duration of stimulation currents for each channel relative to a time reference.

16. The USS of claim 13 wherein the at least five speech processing strategies comprises: a simultaneous analog strategy (SAS), a hybrid analog pulsatile (HAP) strategy, a simultaneous pulsatile strategy (SPS), a multiple pulsatile strategy (MPS), and a non-simultaneous continuous interleaved sampler (CIS) strategy.

17. The USS of claim 16 wherein the selector further includes means for specifying a Number of Maxima (NofM parameter for selected simultaneous SPS or MPS pulsatile strategies, the NofM parameter specifying an integer number (N) of maxima to be used out of a possible number (M) of simultaneous pulsatile channels, wherein the number N defines the number of channels out of the total possible M channels that are simultaneously stimulated with a pulsatile strategy during a prescribed time period.

18. A cochlear stimulation system comprising:

a speech processor having n analysis channels, where n is an integer;

an implantable cochlear stimulator (ICS) having m stimulation channels, where m is an integer less than n;

a first map link for mapping respective ones of the n analysis channels to respective ones of the m stimulation channels;

a second map link for jointly mapping at least one of the n analysis channels jointly to at least two of the stimulation channels; whereby at least one virtual stimulation channel is created via the second map link; and a serial data channel through which information from the n analysis channels is transferred to the ICS in a serial data frame.

19. The cochlear stimulation system of claim 18 wherein the number of n analysis channels comprises at least 20, and wherein the number of m stimulation channels is no greater than 16.

20. The cochlear stimulation system of claim 18 wherein a first of the m stimulation channels adapted for stimulating a basal end of the cochlea, whereat high frequency information is received, is mapped to receive data from a first data word in the serial data frame; and wherein a last of the m stimulation channels adapted for stimulating an apex of the cochlea, whereat low frequency information is received, is mapped to receive data from a last data word in the serial data frame.

21. The cochlear stimulation system of claim 20 wherein the serial data frame comprises a partial data frame wherein at least the last data word is not included in the serial data frame, thereby allowing a faster data update rate to occur through the first data word to the basal end of the cochlea.

22. The cochlear stimulation system of claim 18 further including a switch stage for dynamically enabling or disabling stimulous signals input to at least one of the m stimulous channels.

23. In an implantable cochlear stimulator (ICS) having means for generating both simultaneous analog and non-simultaneous pulsatile stimulation patterns on multiple channels, a method of selecting one of a multiplicity of speech processing strategies, comprising:

(a) displaying a list of the multiplicity of speech processing strategies, wherein a fully simultaneous speech processing strategy is located at one end of the list and a non-simultaneous simultaneous speech processing strategy is located at the other end of the list, and wherein other speech processing strategies are listed in between the fully simultaneous and non-simultaneous simultaneous speech processing strategies as a function of degree of simultaneity;

(b) manually selecting one of the displayed speech processing strategies;

(c) graphically displaying default electrode coupling and waveform diagrams for the manually selected speech processing strategy which illustrate the spatiotemporal relationship between stimulation patterns applied to each channel;

(d) displaying at least one other default parameter associated with the selected speech processing strategy; and (e) generating control signals that define the selected speech processing strategy and sending the control signals to the ICS.

24. The selection method of claim 23 wherein the displayed list of speech processing strategies includes a fully simultaneous analog strategy (SAS), a partially-simultaneous hybrid analog pulsatile (HAP) strategy, a simultaneous pulsatile strategy (SPS), a multiple pulsatile strategy (MPS), and a non-simultaneous continuous interleaved sampler (CIS) strategy.

25. The selection method of claim 24 further including selecting a number of maxima (NofM) parameter for one of a selected SPS, MPS or CIS strategy, the NofM parameter specifying an integer number (N) of maxima to be used out of a possible number (M) of pulsatile channels, wherein the number N defines the number of channels out of the total possible M channels that are stimulated with multiphasic pulses during a prescribed time period.

26. The selection method of claim 24 further including selecting a number of analog channels and pulsatile channels for a selected HAP strategy.

27. In an implantable cochlear stimulator (ICS) having means for generating a plurality of different stimulation patterns on multiple channels, a method of selecting one of a plurality of speech processing strategies, comprising:

(a) displaying a list of the plurality of speech processing strategies;

(b) manually selecting one of the displayed speech processing strategies;

(c) graphically displaying default electrode coupling and waveform diagrams simultaneously for the manually selected speech processing strategy which illustrate the spatiotemporal relationship between stimulation patterns applied to each channel;

(d) displaying at least one other default parameter associated with the selected speech processing strategy; and (e) generating control signals that define the selected speech processing strategy and sending the control signals to the ICS.

28. A method of fitting a cochlear stimulation system to a patient, the cochlear stimulation system including an implantable cochlear stimulator (ICS), an electrode array attached to the ICS, a speech processor (SP) coupled to the ICS, and a microphone coupled to the speech processor; the method of fitting comprising:

(a) coupling an external fitting processor to the SP while the SP remains coupled to the ICS implanted in the patient;

(b) displaying a list of available speech processing strategies;

(c) selecting a potential speech processing strategy from the available speech processing strategies for use by the SP;

(d) displaying the spatiotemporal characteristics of the selected potential speech processing strategy, the spatiotemporal characteristics including a representation of the electrode coupling and a representation of the stimulation waveform simultaneously;

(e) repeating steps (c) and (d), as required, to provide information about each potential speech processing strategy;

(f) selecting one of the potential speech processing strategies as a speech processing strategy to be used by the SP;

(g) generating a first set of control signals within the external fitting processor that cause the selected speech processing strategy to be used by the SP;

(h) applying audio signals to the speech processor through the fitting processor or the microphone and generating second control signals therefrom as a function of the applied audio signals and selected speech processing strategy;

(i) sending the second control signals to the ICS;

(j) applying electrical stimuli to the patient through the electrode array as defined by the second control signals to produce the sensation of sound for the patient;

(k) receiving feedback information from the ICS and/or the patient that characterizes the patient's response to the electrical stimuli applied in step (j) as sensed by the ICS and/or as sensed by the patient;

(l) adjusting the second control signals, as required, in response to the feedback information received in step (k), in order to enhance the ability of the patient to sense the applied electrical stimuli and perceive such as sound;

(m) repeating steps (h) through (k), as required, to improve the patient's ability to sense the audio signals applied in step (h) and correctly perceive the applied audio signals as sound.

29. The method of fitting set forth in claim 28 further including selecting a new speech processing strategy, different from the speech processing strategy initially selected in step (f), and repeating steps (g) through (m) using the new speech processing strategy.

30. A universal strategy selector (USS) for use with a multichannel cochlear prosthesis, the multichannel cochlear prosthesis including multiple stimulation channels through which a specific pattern of electrical stimulation, modulated by acoustic signals, and in accordance with a selected speech processing strategy, may be spatiotemporally applied to various locations within a cochlea in order to yield speech intelligibility, the universal strategy selector comprising:

processing means coupled to the multichannel cochlear prosthesis for defining one of a multiplicity of speech processing strategies for use by the multichannel cochlear prosthesis, at least one of the multiplicity of speech processing strategies comprising a simultaneous speech processing strategy, and at least one other of the multiplicity of speech processing strategies comprising a non-simultaneous speech processing strategy;

a selector associated with the processing means for identifying a selected one of the multiplicity of speech processing strategies as the selected speech processing strategy; and a visual display coupled to the processing means;

wherein the processing means further includes means for controlling the visual display so that a graphical representation appears thereon that characterizes the selected speech processing strategy in terms of representative stimulation waveforms and electrode pairing for each channel.

31. The USS of claim 30 wherein the visual display shows a graphical representation of an electrode array, including electrode contacts on the electrode array, and depicts electrode pairing by appropriate shading or coloring of the electrode contacts.

32. The USS of claim 30 wherein the visual display shows the spatiotemporal relationship of the stimulation waveforms applied to each channel by displaying timing-waveform diagrams of stimulation currents applied to each channel, the timing-waveform diagrams depicting a representation of the duration of stimulation currents for each channel relative to a time reference.

33. The USS of claim 30 wherein the multiplicity of speech processing strategies comprises at least five speech processing strategies including: a simultaneous analog strategy (SAS), a hybrid analog pulsatile (HAP) strategy, a simultaneous pulsatile strategy (SPS), a multiple pulsatile strategy (MPS), and a non-simultaneous continuous interleaved sampler (CIS) strategy.

34. The USS of claim 30 wherein the selector further includes means for specifying a Number of Maxima (NofM) parameter for one of a selected SPS, MPS or CIS strategy, the NofM parameter specifying an integer number (N) of maxima to be used out of a possible number (M) of pulsatile channels, wherein the number N defines the number of channels out of the total possible M channels that are stimulated with biphasic pulses during a prescribed time period.

35. A multichannel cochlear prosthesis comprising:

an electrode array insertable into the cochlea, the electrode array comprising a flexible carrier on which a multiplicity of spaced-apart electrode contacts are positioned, wherein each electrode contact is connected to a respective wire that passes through the carrier to a proximal end of the carrier;

a multichannel implantable cochlear stimulator (ICS), the ICS comprising a multiplicity of current generators, wherein each current generator is connected to a respective electrode contact of the electrode array through the respective wire of the electrode contact, and wherein each current generator includes circuitry responsive to control signals for applying a current pulse of a specified amplitude, polarity and duration to its respective electrode contact;

a speech processor (SP) electronically coupled to the ICS, the SP including electronic circuitry that generates and sends the control signals to the ICS as a function of a selected speech processing strategy and received audio signals;

microphone means for generating the audio signals received by the SP;

wherein the control signals generated by the SP produce a pattern of electrical stimulation at the electrode contacts that yields speech intelligibility; and selection means for selecting one of a multiplicity of speech processing strategies for use within the SP, wherein the multiplicity of speech processing strategies comprises a multiplicity of simultaneous speech processing strategies, including at least one simultaneous analog stimulation (SAS) strategy.

36. A universal strategy selector (USS) for use with a multichannel cochlear prosthesis, the multichannel cochlear prosthesis including multiple stimulation channels through which a specific pattern of electrical stimulation, modulated by acoustic signals, and in accordance with a selected speech processing strategy, may be spatiotemporally applied to various locations within a cochlea in order to yield speech intelligibility, the universal strategy selector comprising:

processing means coupled to the multichannel cochlear prosthesis for defining one of a multiplicity of speech processing strategies for use by the multichannel cochlear prosthesis;

a selector associated with the processing means for identifying a selected one of the multiplicity of speech processing strategies as the selected speech processing strategy; and a visual display coupled to the processing means;

wherein the processing means further includes means for controlling the visual display so that a graphical representation appears thereon that characterizes the selected speech processing strategy in terms of representative stimulation waveforms and electrode pairing for each channel; and wherein the visual display shows a graphical representation of an electrode array, including electrode contacts on the electrode array, and depicts electrode pairing by appropriate shading or coloring of the electrode contacts.

37. The USS of claim 36 wherein the visual display shows the spatiotemporal relationship of the stimulation waveforms applied to each channel by displaying timing-waveform diagrams of stimulation currents applied to each channel, the timing-waveform diagrams depicting a representation of the duration of stimulation currents for each channel relative to a time reference.

38. A cochlear stimulation system comprising:

a speech processor having n analysis channels, where n is an integer;

an implantable cochlear stimulator (ICS) having m stimulation channels, where m is an integer less than n;

a first map link for mapping respective ones of the n analysis channels to respective ones of the m stimulation channels; and a second map link for jointly mapping at least one of the n analysis channels jointly to at least two of the stimulation channels; whereby at least one virtual stimulation channel is created via the second map link;

wherein the number of n analysis channels comprises at least 20, and wherein the number of m stimulation channels is no greater than 16.

* * * * *